(12) United States Patent
Constantz

(10) Patent No.: US 6,622,732 B2
(45) Date of Patent: *Sep. 23, 2003

(54) METHODS AND DEVICES FOR REDUCING THE MINERAL CONTENT OF VASCULAR CALCIFIED LESIONS

(75) Inventor: Brent R. Constantz, Palo Alto, CA (US)

(73) Assignee: Corazon Technologies, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/091,133

(22) Filed: Mar. 4, 2002

(65) Prior Publication Data

US 2003/0018297 A1 Jan. 23, 2003

Related U.S. Application Data

(63) Continuation of application No. 09/353,127, filed on Jul. 14, 1999, now Pat. No. 6,379,345, which is a continuation-in-part of application No. 09/195,291, filed on Nov. 18, 1998, now Pat. No. 6,387,071, which is a continuation-in-part of application No. 09/118,193, filed on Jul. 15, 1998, now Pat. No. 6,394,096.

(51) Int. Cl.[7] .............................................. A61B 19/00
(52) U.S. Cl. ......................................... 128/898; 604/28
(58) Field of Search ....................... 128/898; 604/27–28, 604/27.43, 43

(56) References Cited

U.S. PATENT DOCUMENTS

| | | | |
|---|---|---|---|
| 3,651,868 A | 3/1972 | Caudle et al. | 166/307 |
| 3,855,914 A | 12/1974 | Nishino et al. | 99/275 |
| 3,860,289 A | 1/1975 | Learmont | 299/4 |
| 4,022,119 A | 5/1977 | Karr | 99/275 |
| 4,049,519 A | 9/1977 | Sloan | 204/180 |
| 4,105,253 A | 8/1978 | Showalter | 299/4 |
| 4,108,764 A | 8/1978 | Kaneko et al. | 210/22 A |
| 4,250,965 A | 2/1981 | Wiseman, Jr. | 166/305 R |
| 4,358,158 A | 11/1982 | Showalter | 299/4 |
| 4,445,892 A | 5/1984 | Hussein et al. | 604/101 |
| 4,573,966 A | 3/1986 | Weikl et al. | 604/53 |
| 4,610,662 A | 9/1986 | Weikl et al. | 604/53 |
| 4,636,195 A | 1/1987 | Wolinsky | 604/53 |
| 4,655,746 A | 4/1987 | Daniels et al. | 604/53 |
| 4,705,517 A | 11/1987 | DiPisa, Jr. | 623/12 |
| 4,778,006 A | 10/1988 | Derowitsch | 166/267 |
| 4,824,436 A | 4/1989 | Wolinsky | 604/53 |
| 4,850,975 A | 7/1989 | Furukawa | 604/170 |
| 4,883,460 A | 11/1989 | Zanetti | 604/22 |
| 4,911,163 A | 3/1990 | Fina | 606/127 |
| 4,976,733 A | 12/1990 | Giradot | 623/11 |
| 5,059,178 A | 10/1991 | Ya | 604/101 |
| 5,069,664 A | 12/1991 | Guess et al. | 604/22 |
| 5,090,960 A | 2/1992 | Don Michael | 604/101 |

(List continued on next page.)

FOREIGN PATENT DOCUMENTS

| | | |
|---|---|---|
| WO | 97/40756 | 11/1997 |
| WO | 98/25855 | 6/1998 |

*Primary Examiner*—Corrine McDermott
*Assistant Examiner*—Thomas Barrett
(74) *Attorney, Agent, or Firm*—Bret E. Field; Bozicevic, Field & Francis

(57) ABSTRACT

Methods and devices are provided for at least reducing the mineral content of a vascular calcified lesion, i.e. a calcified lesion present on the vascular tissue of a host. In the subject methods, the local environment of the lesion is maintained at a subphysiologic pH for a period of time sufficient for the mineral content of the lesion to be reduced, e.g. by flushing the lesion with a fluid capable of locally increasing the proton concentration in the region of the lesion. Also provided are systems and kits for practicing the subject methods. The subject methods and devices find particular use in the treatment of vascular diseases associated with the presence of calcified lesions on vascular tissue.

7 Claims, 5 Drawing Sheets

U.S. PATENT DOCUMENTS

| | | | |
|---|---|---|---|
| 5,135,484 A | * 8/1992 | Wright | 604/28 |
| 5,140,822 A | 8/1992 | Gupta | 62/50.1 |
| 5,167,628 A | 12/1992 | Boyles | 604/101 |
| 5,171,694 A | 12/1992 | Connolly | 436/134 |
| 5,195,955 A | 3/1993 | Don Michael | 604/22 |
| 5,222,941 A | 6/1993 | Don Michael | 604/101 |
| 5,238,845 A | 8/1993 | Tancredi et al. | 436/8 |
| 5,380,284 A | 1/1995 | Don Michael | 601/101 |
| 5,443,446 A | 8/1995 | Shturman | 604/49 |
| 5,462,529 A | 10/1995 | Simpson et al. | 604/101 |
| 5,681,507 A | 10/1997 | Kazuma | 261/27 |
| 5,702,368 A | 12/1997 | Stevens et al. | 604/171 |
| 5,735,811 A | * 4/1998 | Brisken | 604/22 |
| 5,736,072 A | 4/1998 | Satoh | 261/27 |
| 5,758,789 A | 6/1998 | Shin et al. | 215/382 |
| 5,833,650 A | 11/1998 | Imran | 604/53 |

* cited by examiner

METHODS AND DEVICES FOR REDUCING THE MINERAL CONTENT OF VASCULAR CALCIFIED LESIONS

CROSS-REFERENCE TO RELATED APPLICATIONS

This application is a continuation-in-part of application Ser. No. 09/195,291,now U.S. Pat. No. 6,387,071 filed Nov. 18, 1998; which application is a continuation-in-part of application Ser. No. 09/118,193 now U.S. Pat. No. 6,394,096 filed on Jul. 15, 1998; the disclosures of which are herein incorporated by reference.

INTRODUCTION

1. Technical Field

The field of this invention is vascular disease, particularly vascular diseases characterized by the presence of calcified lesions, e.g. atherosclerosis, and the like.

2. Background of the Invention

The formation of plaques or lesions, (atherosclerotic plaques or lesions) on cardiovascular tissue, such as the inner surface of blood vessels, aortic valves, etc., is a major component of cardiovascular disease. Many atherosclerotic plaques and lesions are characterized by the presence of mineral deposits, i.e. they are calcified. Calcified lesion formation on prosthetic devices is also a problem in current cardiovascular disease treatment protocols. For example, calcification is an important limitation on the useful life expectancy of bioprosthetic valves, and accounts for over sixty percent of the cardiac bioprostheses failures.

A variety of different protocols have been developed for treating cardiovascular diseases associated with the presence of calcified lesions. Such treatment methodologies generally involve mechanical removal or reduction of the lesion, and include: bypass surgery, balloon angioplasty, mechanical debridement, atherectomy, valve replacement, and the like. Despite the plethora of different treatment strategies that have been developed for the treatment of cardiovascular disease, there are disadvantages associated with each technique, such as tissue damage, invasiveness, etc. For example, restenosis is a common complication that results in arteries in which lesions have been mechanically removed.

As such, there is continued interest in the development of new treatment protocols for the removal of vascular calcified lesions from vascular tissue. Of particular interest would be the development of a treatment protocol that is minimally invasive and/or results in minimal tissue damage.

Relevant Literature

U.S. Patents of interest include: U.S. Pat. Nos. 4,445,892; 4,573,966; 4,610,662; 4,636,195; 4,655,746; 4,824,436; 4,911,163; 4,976,733; 5,059,178; 5,090,960; 5,167,628; 5,195,955; 5,222,941; 5,380,284; 5,443,446; and 5,462,529.

SUMMARY OF THE INVENTION

Methods for at least reducing the mineral content of a calcified lesion on vascular tissue are provided. In the subject methods, the local environment of the target lesion is maintained at a subphysiologic pH for a period of time sufficient for the desired amount of demineralization to occur, e.g. by flushing the lesion with a fluid capable of locally increasing the proton concentration in the region of the calcified lesion. As a result, the mineral content of the calcified lesion is reduced. Also provided are kits and systems for practicing the subject methods. The subject invention finds use in a variety of different applications, including the treatment of vascular diseases associated with the presence of calcified lesions.

DESCRIPTION OF THE SPECIFIC EMBODIMENTS

Figure 1:
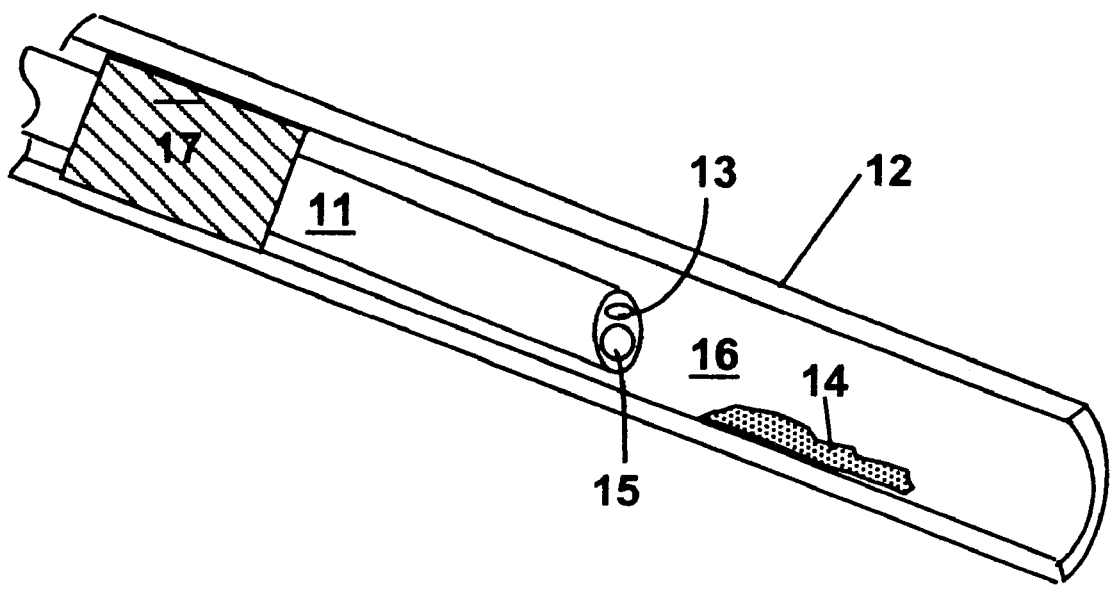
FIG. 1 provides a cutaway view of a vessel being treated according to one embodiment of the subject invention.

Methods are provided for at least reducing the mineral content of a calcified lesion on vascular structure, e.g. vascular tissue, vascular prosthetic implant, etc. In the subject methods, the local environment of the calcified lesion is maintained at a subphysiological pH for a sufficient period of time for the desired amount of demineralization to occur, e.g. by flushing the lesion with a fluid capable of locally increasing the proton concentration in the region of the lesion. The subject methods find use in the treatment of vascular diseases characterized by the presence of calcified vascular structure calcified lesions. Also provided are kits and systems for use in performing the subject methods. In further describing the subject invention, the subject method is discussed first, both in general terms and in terms of specific representative applications. This discussion is then followed by a description of systems and kits for use in practicing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Methods

The invention provides a method for at least reducing the mineral content of a vascular calcified lesion by contacting the lesion with a fluid capable of locally increasing the proton concentration in the region of the lesion. As used herein, the term "vascular" is used broadly to refer to the circulatory system of an organism. As such, the term "vascular" refers to arteries and veins, as well as specialized organs that are closely associated with the circulatory system, such as the heart. The term "cardiovascular" refers to that portion of the vascular system that is closely associated with the heart. Thus, target lesions of the subject methods are vascular calcified lesions, including cardiovascular calcified lesions.

A lesion is considered to be a vascular calcified lesion if it is present on a vascular structure. Vascular structures include vascular tissues as well as vascular implants positioned within the vascular system. Vascular tissue refers to any tissue that is present in the circulatory system of the host, as described above, and as such includes not only vessel tissue, such as arterial and venous tissue, but also cardiac or heart tissue, including valves and other cardiovascular features or specialized tissue structures. Vascular implants include prosthetics that have been introduced into the vascular system, including bioprosthetics, etc, such as allogeneic and xenogeneic implants, e.g. heart valves, synthetic implants, vascular replacements or grafts, e.g. saphenous vein grafts, artificial hearts, left ventricular assist devices, electrodes, and the like. Thus, vascular structures include both naturally occurring vascular tissue and implants of exogenous origin that have been introduced into the circulatory system.

The vascular structure on which the target calcified lesion is present is a structure found on the blood side of the circulatory system, by which is meant that the structure is found on the side of the circulatory system adjacent to blood flow and which comes into contact with blood, and not on the outside of the circulatory system, i.e. that portion of the circulatory system that does not contact blood. As such, the lesion may be present on: (a) the inner wall or intima of a blood vessel; (b) a valve present in a blood vessel; (c) a heart valve; (d) an implant present in an artery or vein; etc.

Calcified Target Lesion

The calcified target lesion may be a substantially pure mineral deposit or coating over the surface of a region of vascular tissue, such as a coating or layer on at least a portion of valve tissue and the like, or may be a more complex formation that includes both mineral and other components, including organic matter, e.g. lipids, proteins, and the like.

The mineral component making up the calcified lesion is generally made up of one or more calcium phosphates, where the calcium phosphates are generally apatitic. The term "apatite" as used herein refers to a group of phosphate minerals that includes ten mineral species and has the general formula $X_5(YO_4)_3Z$, where X is usually $Ca^{2+}$ or $Pb^{3+}$, Y is $P^{5+}$ or $As^{5+}$, and Z is $F^-$, $Cl^-$, or $OH^-$. The term calcium apatite refers to a group of phosphate minerals where X is $Ca^{2+}$. The mineral component of the calcified lesion typically includes one or more of hydroxyapatite, carbonated hydroxyapatite (dahllite) and calcium deficient hydroxyapatite.

In addition to the mineral component, the lesion that is the target of the subject methods may also comprise one or more additional components, where such components include: lipids; lipoproteins; proteins; including fibrinogen, collagen, elastin and the like; proteoglycans, such as chondroitin sulfate, heparin sulfate, dermatans, etc.; and cells, including smooth muscle cells, epithelial cells, macrophages and lymphocytes. As such, calcified lesions that are targets of the subject methods include: type IV, type V and type VI lesions, as defined in Stary et al., Arterioscler Thromb Vasc Biol. (1995)15:1512–1531.

In arterial lesions that are targets of the subject methods, the mineral component of the calcified lesion generally makes up from about 10 to 100, usually from about 10 to 90 and more usually from about 10 to 85 dry weight % of the lesion. The size of the lesion that is the target of the subject methods varies depending on whether it is a lesion found in arteries, in the aorta or on a valve, e.g. a heart valve. As such, the size of the lesion may vary substantially, but will typically cover an area, e.g. surface of arterial intima, of at least about 1 mm$^2$, usually at least about 4 mm$^2$ and more usually at least about 10 mm$^2$, where the area covered by the lesion may be as large as 40 mm$^2$ or larger, but will usually not exceed about 20 mm$^2$, and more usually will not exceed about 15 mm$^2$.

Maintaining the Local Environment of the Lesion at a Subphysiologic pH

As summarized above, the mineral content of vascular calcified target lesions (as described above) is reduced according to the subject invention by maintaining the local environment of the lesion at a subphysiological pH for a sufficient period of time for the desired amount of demineralization to occur. By local environment of the lesion is meant the immediate vicinity of the lesion, such as the area defined by a set distance from any surface point (i.e. point not adjacent or juxtaposed to the vesicular tissue, e.g. intima, with which the lesion is associated) on the lesion, typically extending at least 1 mm$^2$, usually at least 2 mm$^2$ beyond the area covered by the lesion, and in many embodiments substantially further beyond the area covered by the lesion. For example, where the target lesion covers a 4 mm$^2$ surface of arterial intima, the local environment will extend to cover an area of 6 mm$^2$. In three-dimensional terms, where a lesion occupies a volume of 8 mm$^3$, the volume of the local environment will be at least 9 mm$^3$ and will often be larger. In many embodiments, the local environment may extend beyond this limited area. For example, the local environment may be a mechanically isolated section of a vessel or valve in which the lesions are present, where the volume of such an isolated section may range from about 4 to 4000 mm$^3$, usually from about 40 to 2000 mm$^3$ and more usually from about 100 to 1000 mm$^3$. Furthermore, the local environment may be an isolated limb or portion thereof. In yet other embodiments, the local environment may be a given length of a blood vessel, e.g. an artery, that has been cannulated on either side of the lesion (e.g. in those embodiments where the target lesion is a diffuse lesion that extends for a given length of the blood vessel). In certain embodiments, the volume of the local environment of the lesion ranges from about 1 to 100, usually from about 5 to 50 and more usually from about 10 to 20 fold greater than the volume of the lesion, where the local environment volume includes the volume of the lesion. In other embodiments, the local environment includes a defined area adjacent to only one side of the target lesion, e.g. where the target lesion is a substantially complete vascular occlusion. In such embodiments, the local environment will not necessarily be larger that the total volume of the target lesion, but will instead merely include the region of the vessel volume adjacent to one surface of the vascular occlusion. Importantly, however, the local region does not include the entire vascular system. As such, the local environment of lesion is less than 90%, usually less than 80% and more usually less than 50% of the entire volume (e.g. the volume of circulating blood) of the vascular system of the host or subject being treated. In many embodiments, the local environment is less than 5% and typically between about 1 to 2% of the entire volume of the vascular system of the host.

Preferably, the local environment of the lesion is at least substantially bloodless, by which is meant that the local environment contains substantially no blood components, particularly red blood cells, white blood cells, platelets, serum proteins, e.g. albumin, and the like. By substantially bloodless is meant that the local environment includes less than 75%, usually less than 50% and more usually less than 25% of the blood components originally present in the local environment (where percentage is based on dry weight), where the number of originally present blood components in the local environment is preferably less than 20%, more preferably less than 15% and most preferably less than 10%. The local environment is rendered substantially bloodless using any convenient methodology, where representative methodologies are provided infra.

As mentioned above, the pH in the local environment is maintained at a subphysiological level for a sufficient period of time for the desired amount of demineralization of the target lesion to occur. Typically, the pH is maintained at a value that does not exceed about 5 and usually does not exceed about 4, and more usually does not exceed about 3. In many embodiments, the pH of the dissolution solution ranges from between 0 and 1. Within the above range, the pH may be constant or variable over the course of the demineralization procedure, i.e. over the period of time during which the pH of the local environment is maintained at a subphysiological value.

The time period during which the local pH is maintained at a subphysiological level in the local region of the lesion is sufficient for the desired amount of demineralization to occur. As such, the pH of the local environment is maintained at a subphysiological value for a period of time ranging from about 5 to 200 minutes, usually from about 10 to 100 minutes and more usually from about 10 to 30 minutes.

The pH of the local environment in the region of the lesion may be maintained at the requisite subphysiological level using any convenient protocol. Where a substantially constant subphysiological level is desired, a dynamic introduction of the fluid into the local environment is employed. Alternatively, where some variability in the pH of the local environment is acceptable, a static introduction of the fluid into the local environment may be employed. Dynamic and static introduction methods are described in greater detail infra. Of particular interest in many embodiments is the use of a dissolution solution that is introduced into the local environment of the lesion and is capable of locally increasing the proton concentration in the local environment of the lesion. By capable of locally increasing the proton concentration is meant that the dissolution solution, upon introduction into the local environment of the lesion, as described in greater detail below, is capable of increasing the hydrogen ion concentration or [$H^+$] in the region of the lesion. In other words, the solution is capable of reducing the pH in the region of the lesion to the requisite subphysiologic level for the required demineralization to occur.

As mentioned above, in preferred embodiments, the local environment of the lesion is substantially, if not completely, bloodless. As such, the method of the subject invention typically includes a step of rendering the local environment of the lesion at least substantially bloodless. Any means of rendering the local environment bloodless may be employed, such as the use of devices with balloons, cannulation devices, and the like, where representative methods of rendering the local environment of the target lesion substantially bloodless are described in further detail infra.

Dissolution Solutions

A variety of different types of dissolution solutions may be employed in the subject methods, as long as the solutions are capable of increasing the proton concentration locally in the region of the target lesion to the desired subphysiologic level. In other words, any solution that is capable of providing the requisite subphysiologic pH in the local environment of the lesion is suitable for use in the subject methods. Instead of using a single dissolution solution, a plurality of different dissolution solutions which vary by one or more parameters (e.g. type, pH, concentration etc.) may be sequentially introduced into the region of the lesion. In such embodiments, the number of different dissolution solutions employed is at least 2, but generally does not exceed about 4 and usually does not exceed about 3.

One type of solution that finds use is an acidic dissolution or treatment solution. The acidic treatment solution will generally have a pH of less than about 6.5, where the pH is usually less than about 4.0 and more usually less than about 3.0. In many preferred embodiments, the pH ranges from 0 to 2, and usually 0 to 1. The acidic treatment solution can include a number of different types of acids, where the acids may or may not include a hydrocarbon moiety, i.e. a hydrogen bonded direction to a carbon atom. Suitable acids that lack a hydrocarbon moiety include halogen acids, oxy acids and mixtures thereof, where specific acids of interest of this type include, but are not limited to, hydrochloric, nitric, sulfuric, phosphoric, hydroboric, hydrobromic, carbonic and hydroiotic acids. For such acids, the acid can be a concentrated acid, or can be diluted. Upon dilution, the concentration of an inorganic acid will generally be from about 10 N to about 0.01 N, preferably between 5 N to 0.1 N. Also of interest are acids that include a hydrocarbon moiety, where such acids include, but are not limited to, any organic acid of one to six ($C_1$ to $C_6$) carbons in length. Organic acids of this type include, but are not limited to, formic, acetic, propionic, maleic, butanoic, valeric, hexanoic, phenolic, cyclopentanecarboxylic, benzoic, and the like. For an organic acid, the acid can be in concentrated form, or can be diluted. The acidic treatment solution can be composed of either a monobasic or a polybasic acid. Acids are "monobasic" when they have only one replaceable hydrogen atom and yield only one series of salts (e.g., HCl). Acids are "polybasic" when they contain two or more hydrogen atoms which may be neutralized by alkalies and replaced by organic radicals.

In many embodiments of the subject invention, the acid solution is hypertonic, by which is meant that the osmolarity of the solution is greater than that of a red blood cell, i.e. the osomolarity is greater than 300 mosmol. The solution may be rendered hypertonic by including any convenient component or components in the solution which provide for the desired elevated osmolarity.

Any convenient agent that is capable of increasing the osmolarity of the solution may be employed, where suitable agents include salts, sugars, and the like. In many embodiments, the agent that is employed to render the solution hypertonic is one or more, usually no more than three, and more usually no more than two, different salts. Generally, the salt concentration in these embodiments of the solution is at least about 100 mosmol, usually at least about 200 mosmol and more usually at least about 300 mosmol, where the concentration may be as high as 3000 mosmol or higher, depending on the particular salt being employed to render the solution hypertonic, where the solution may be saturated with respect to the salt in certain embodiments. Salts that may be present in the subject solutions include: NaCl, $MgCl_2$, Ringers, etc. where NaCl is preferred in many embodiments.

Two acid solutions of particular interest are hydrogen chloride solutions and carbonic acid solutions. Each of these is discussed in greater detail below.

Hydrogen Chloride Solutions

Hydrogen chloride solutions finding use in the subject methods have an HCl concentration that is sufficient to provide for the requisite pH in the local environment of the target lesion. Generally, the concentration of HCl in the solution ranges from about 0.001 to 1.0 N, usually from about 0.01 to 1.0 N and more usually from about 0.1 to 1.0 N. In many embodiments, the hydrogen chloride solution will further include one or more salts which make the solution hypertonic, as described above. In certain preferred embodiments, the salt is NaCl, where the concentration of NaCl in the solution is at least 0.05 M, usually at least 0.10 M, and more usually at least 0.15 M, where the concentration may be as high as 0.25 M or higher. In certain embodiments, the solution will be saturated with NaCl.

Carbonic Acid Solutions

In another preferred embodiment of the subject invention, the solution that is employed is a carbonic acid solution. Carbonic acid solutions that find use are aqueous solutions that have a pH that is sufficiently low to achieve the desired subphysiological pH in the local region of the lesion during treatment. As such, the pH of the carbonic acid solution is typically less than about 6, usually less than about 5 and more usually less than about 4, where the pH may be as low as 2 or lower, but will generally not be below about 1. The carbonic acid concentration of the solution may vary, but will generally range from about 0.1 to 4.0 M and usually from about 0.1 to 1.0 M. The carbonic acid solution should be bubble free, i.e. $CO_2$ bubble free, during use. As such, the pressure and/or temperature of the carbonic acid solution may be modulated to provide the requisite bubble free properties. The carbonic acid solution may be at ambient or elevated pressure, i.e. pressurized. Where the carbonic acid solution is pressurized, it will be pressurized to at least about 10 bar (10 atm), usually at least about 50 bar and more usually to at least about 100 bar, where it may be pressurized to a pressure of 1000 bar or greater. The temperature of the carbonic acid solution may vary from about 0 to 37° C., usually from about 10 to 37° C. and more usually from about 20 to 37° C.

The carbonic acid solution may be produced in a number of different ways. For example, the carbonic acid solution may be prepared by combining sodium bicarbonate and hydrogen chloride solutions in a manner sufficient to produce a carbonic acid solution. The sodium bicarbonate solution that is employed will generally have a sodium bicarbonate concentration ranging from about 0.01 to 1.0 M, and usually from about 0.02 to 0.1 M. The hydrogen chloride solution that is employed will have a concentration ranging from about 0.01 to 1.0 M and usually from about 0.01 to 0.5 M. Upon combination of the sodium bicarbonate solution and hydrogen chloride solution, carbonic acid is produced in accordance with the following equilibrium equation:

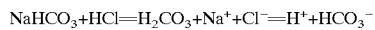
$$NaHCO_3 + HCl \rightleftharpoons H_2CO_3 + Na^+ + Cl^- \rightleftharpoons H^+ + HCO_3^-$$

The equilibrium of the above reaction is maintained in favor of production of the proton by maintaining the pressure and temperature of the solution at appropriate values. For a solution prepared in this manner, the pressure of the solution is maintained in a range of from about 10 to 200 bar and usually from about 50 to 150 bar while the temperature is maintained at a value ranging from about 0 to 37° C. and usually from about 20 to 37° C.

The carbonic acid solution that finds use in the subject invention can also be produced by making an aqueous solution that is saturated with respect to $CO_2$. In this embodiment, the solution is maintained as bubble free, by which is meant that $CO_2$ gas is prevented from coming out of solution such that the carbonic acid equilibrium reaction:

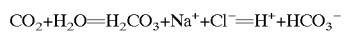
$$CO_2 + H_2O \rightleftharpoons H_2CO_3 + Na^+ + Cl^- \rightleftharpoons H^+ + HCO_3^-$$

is driven in the direction of carbonic acid, i.e. $H_2CO_3$, and consequently proton and bicarbonate ion production. Generally, the $pCO_2$ in this carbonic acid solution is at least about 100, usually at least about 500 and more usually at least about 1000 mmHg, where the $pCO_2$ of the solution may be as high as 5000 mmHg or higher, but will generally not exceed about 10,000 mmHg. The solution prior to delivery will typically be pressurized to some pressure above atmospheric pressure such that it remains bubble free and yet saturated, even supersaturated, with respect to the $CO_2$. As such, the pressure of the solution is generally at least about 10 bar, usually at least about 50 bar and more usually at least about 100 bar, where the pressure may be as high as 200 bar or higher, but will generally not exceed about 1000 bar. The temperature of the solution may also be modulated to obtain the desired dissolved $CO_2$ in the solution. As such, the temperature may range from about 0 to 37° C., usually from about 10 to 37° C. and more usually from about 20 to 37° C. A variety of technologies are known to those of skill in the art for producing aqueous solutions that are saturated with respect to $CO_2$, any of which may be employed to produce the carbonic acid solution finding use in the subject methods. Of particular interest are the techniques disclosed in U.S. Pat. Nos. 5,086,620; 5,261,875; 5,407,426; 5,599,296; 5,569,180; 5,693,017; 5,730;935; 5,735,934; and 5,797,874; the disclosures of which applications are herein incorporated by reference. Briefly, a stable, bubble-free saturated $CO_2$ aqueous solution is produced by contacting gaseous $CO_2$ with an aqueous carrier medium, e.g. pure water, under elevated pressure conditions such that the gaseous $CO_2$ goes into, and is maintained in, solution.

Additional Components

The dissolution solutions employed in the subject invention may also comprise one or more additional components that serve a variety of purposes. Components that may be included are ions which serve to: (a) prevent apatite formation, (b) prevent apatite reformation, (c) modify apatite solubility, etc., where such ions include $Mg^{2+}$, and the like. When present, the concentration of the magnesium ion in the solution will generally range from about 0.01 to 0.20 M, usually from about 0.05 to 0.1 M.

The solution may further include an oxygenating medium for delivery of oxygen to the local environment of the lesion during treatment, i.e. the solution may further comprise oxygen—the solution may be supersaturated with respect to $O_2$. When present, the solution will comprise 1 to 4, usually 1 to 3 ml $O_2$/g fluid. Any convenient oxygenating medium may be employed, including the hyperbaric oxygen mediums disclosed in U.S. Pat. Nos. 5,086,620; 5,261,875; 5,407,426; 5,599,296; 5,569,180; 5,693,017; 5,730;935; 5,735,934; and 5,797,874, the disclosures of which are herein incorporated by reference. An example of situations where oxygenating mediums find use in the dissolution solution include the treatment of diffuse arterial lesions by the subject methods, e.g. diffuse arterial lesions found in the limbic extremities. For example, to treat a lower limbic extremity diffuse arterial lesion, e.g. an arterial lesion present below the knee, one can produce an isolated local environment by blocking the appropriate artery (e.g. posterior tibial artery, anterior tibial artery) and vein (e.g. great saphenous vein, small saphenous vein) on either side of the diffuse lesion. The lesion can then be contacted, e.g. flushed, with the dissolution solution comprising the oxygenating medium by introducing the solution into the artery and removing it from the vein, as described in greater detail below. In this embodiment, the entire circulatory system below the substantially blocked portions of the artery and vein is transformed into the local environment of the lesion in which a subphysiologic pH is maintained. The oxygenating medium serves to maintain the requisite oxygen levels in the tissue of the local environment of the lesion.

The dissolution treatment solution can further include calcium-chelating agents, for example, EDTA, crown ethers, and the like. The concentration of these agents will vary, but will generally not exceed about 4.0 M and usually will not exceed about 1.0 M.

The dissolution solution may also include an enzymatic component that serves to promote the formation of protons in the solution and local environment of the lesion in order to provide for the subphysiologic pH. A variety of enzymes or activities may be employed, depending on the specific nature of the dissolution solution. For example, in those embodiments in which the dissolution solution is saturated with $CO^2$ gas, the solution can further include carbonic anhydrase. The enzyme may be a naturally occurring enzyme or synthetic homologue thereof, where the enzyme may be produced via purification from naturally occurring sources or through recombinant technology.

In addition, the dissolution solution may further include one or more components which act on the non-mineral phase of the target lesion in order to disrupt the lesion and promote its disruption and/or dissolution. Such, organic disruption/dissolution agents that may be present in the dissolution solution include: thrombolytic agents, e.g. urokinase, tPA, etc.; enzymes, e.g. proteases, collegenases; heparin; surfactants; detergents; etc.

Contacting the Calcified Target Lesion with the Dissolution Solution

As mentioned above, in the subject methods the dissolution solution is introduced into the local environment of the lesion in a manner sufficient to maintain the pH of the local environment of the lesion at the requisite subphysiological level for a sufficient period of time for the desired amount demineralization to occur. As such, the subject methods generally involve contacting the lesion with the dissolution solution. The manner in which contact is achieved-may be static or dynamic. By static is meant that a predetermined amount of dissolution solution is introduced into the local environment of the lesion and maintained in the local environment of the lesion for the entire treatment period, without the addition of further quantities of dissolution solution. By dynamic is meant that the dissolution solution is introduced into the local environment of the lesion one or more times, including continuously, during the treatment period. As mentioned above, the local environment of the lesion has preferably been rendered bloodless prior to introduction of the dissolution fluid.

During the dissolution procedure, protons from the local environment are removed as a result of the demineralization process. As such, it is often desirable to introduce the dissolution solution into the local environment of the lesion in a dynamic manner. Dynamic introduction of the dissolution solution typically involves flushing the lesion with the dissolution solution, where flushing involves a continuous flow of the dissolution solution across at least a surface of the lesion, where the flow may be under pressure (e.g. where the fluid is emitted from the delivery device under enhanced pressure, as described in greater detail infra). In other words, the dissolution fluid is continuously flowed through the local environment of the lesion for the period of time required for the desired amount of demineralization to occur. Simultaneously, fluid is removed from the local environment of the lesion such that the overall volume of fluid in the local environment of the lesion remains substantially constant, where any difference in volume at any two given times during the treatment period does not exceed about 50%, and usually does not exceed about 10%. In this manner, the pressure of the localized environment of the lesion is maintained at a substantially constant value, thereby minimizing traumatic impact on the vessel walls in the region of the lesion.

Where the lesion is flushed with the dissolution solution, the flow rate of the dissolution solution through the local environment of the lesion is generally at least about 1 volume/minute, usually at least about 2 volumes/minute and more usually at least about 10 volumes/minute, where the flow rate may be as great as 100 volumes/minute or greater, but usually does not exceed about 1000 volumes/minute and more usually does not exceed about 500 volumes/minute, where by "volume" is meant the volume of the local environment of the lesion.

When treatment involves dynamic flushing of the local environment of the lesion, the total amount of dissolution fluid that is passed through the local environment of the lesion during the treatment period typically ranges from about 0.5 to 50 liters, usually from about 0.5 to 5.0 liters and more usually from about 0.5 to 2.0 liters. In contrast, where a static methodology is employed, the total amount of dissolution fluid that is introduced into the local environment of the lesion ranges from about 100 ml to 1 liter, and usually from about 100 to 500 ml.

Devices for Contacting the Target Lesion with the Dissolution Solution

Any convenient means may be employed for introducing the dissolution solution into the local environment of the lesion. In general, the dissolution fluid introduction means should at least include a means for introducing dissolution fluid into the local environment of the lesion. Typically, the means is a conduit, e.g. tube, which has an opening at its distal end (i.e. the end that comes closest to the lesion during use) and is in fluid communication at its proximal end with a container holding the dissolution fluid, where the fluid communication relationship can be established through direct contact of the lumen with the container or through one or more connecting means which establish the requisite fluid communication.

In many embodiments, e.g. where the lesion is flushed with the dissolution solution, contact also includes removal of solution from the local environment of the lesion. Any convenient means may be employed for removing dissolution solution, as well as particles of lesion and dissolved lesion components, from the local environment of the lesion. The fluid removal means may be incorporated into the fluid introduction means summarized above or a separate component from the fluid introduction means. Thus, fluid removal means may be a conduit or vessel which is a component of the fluid introduction means, or may be a conduit or vessel on a separate catheter, cannula etc, which is positioned "downstream" in the direction of blood flow from the target lesion and the site of introduction of the dissolution fluid.

In many embodiments, the fluid introduction means is a catheter. In many embodiments, catheters employed in the subject methods include at least one fluid introduction means for introducing a dissolution fluid to the local environment of the lesion and a fluid removal means for removing fluid from the local environment of the lesion. In many embodiments, the catheter devices of the subject invention also typically include a means for isolating the local environment of the target lesion.

As mentioned above, the dissolution fluid introduction means is generally a lumen having a proximal end in fluid communication with the dissolution fluid source, e.g. a dissolution fluid reservoir, and an open distal end capable of being introduced into the local environment of the target lesion. By "lumen" is meant an elongated vessel having a tubular structure with a proximal and distal end, where the cross-sectional shape along the length of structure is generally (though not necessarily) circular, ovoid or some other curvilinear shape. The dissolution fluid introduction lumen has sufficient dimensions to allow for the desired flow rate at the site of the target lesion. The exact dimensions for the fluid introduction lumen will vary depending, at least in part, on the nature of the dissolution fluid that is to be introduced in the region of the lesion. For example, with HCl solutions, fluid introduction lumens having inner diameters (ID) ranges from about 1 to 5 mm, usually from about 1 to 3 mm and more usually from about 1 to 2 mm are typically employed. Alternatively, in those embodiments in which a pressurized dissolution fluid is delivered to the local environment of the lesion, e.g. where a carbonic acid solution is employed as the dissolution solution, the dimensions are often sufficient to reduce bubble formation, e.g. $CO_2$ bubble formation. As such, the dissolution fluid introduction lumen has an inner diameter (ID) that is at least about 50 $\mu$m, usually at least about 100 $\mu$m and more usually at least about 200 $\mu$m, where the inner diameter will typically not exceed about 2000 $\mu$m and usually will not exceed about 1000 $\mu$m. Depending on the configuration of the catheter device, the entire cross-sectional area may be available for fluid flow, or a portion of the cross-sectional area may be occupied by one or more additional device elements, e.g. a guide wire, one or more additional lumens, and the like, as described in greater detail infra. The fluid introduction lumen may be fabricated from a wide variety of materials. See the patents listed in the relevant literature section, supra. In those embodiments where the dissolution fluid is pressurized, as described above, the lumen is fabricated from materials capable of preserving the pressure of the fluid. Such materials are described in U.S. Pat. Nos. 5,599,296; 5,569,180; 5,693, 017; 5,730;935; 5,735,934; and 5,797,874; the disclosures of which applications are herein incorporated by reference. Also of interest are multiple small lumens having ID of between about 50 and 80 $\mu$m, usually around 75 $\mu$m.

In addition to the fluid introduction means, the subject catheters typically further include a fluid removal means capable of removing fluid from the local region or environment of the lesion. A critical feature of the fluid removal means in many embodiments is that it is capable of removing fluid from the local environment of the lesion at the same rate as that at which fluid is introduced into the local environment of the lesion by the dissolution fluid introduction means. The fluid removal means is typically a lumen having dimensions that allow for adequate fluid flow from the local environment of the target lesion. In addition, in certain embodiments the dimensions of the second lumen are such that they allow passage of the debris from the local environment of the lesion through the second lumen. In such embodiments, the fluid removal lumen has an inner diameter that is substantially longer than the inner diameter of the fluid introduction lumen, where by substantially longer is meant at least about 2 fold longer, usually at least about 5 fold longer. As such, the fluid removal lumen typically has an inner diameter that is at least about 1 mm, usually at least about 2 mm and more usually at least about 3 mm, where the inner diameter typically does not exceed about 5 mm and usually does not exceed about 4 mm. The fluid removal lumen may be fabricated from any suitable material, where a variety of suitable materials are known to the those of skill in the art.

In many embodiments, the subject device further includes a means for substantially isolating the local environment of the lesion from the remainder of the host's circulatory system so that the local environment can be rendered substantially, if not completely, bloodless. By substantially isolating is meant that fluid communication between the local environment of the lesion and the remainder of the host's circulatory system is essentially removed—i.e. the local environment of the lesion is no longer accessible by fluid from the remainder of the host's circulatory system or vice versa. Any convenient means may be employed for isolating the local environment of the lesion. Such means include "cup" components that snugly fit over the lesion and thereby isolate it from the remainder of the circulatory system, dual balloon systems that inflate on either side of the lesion to isolate the local environment, etc.

In addition to the above components, the capillary devices of the subject invention may further include: (a) one or more additional lumens, e.g. for introducing a rinse or wash fluid to the local environment of the lesion; a means for allowing blood to flow through the isolated local environment, e.g. a pass through lumen; a means for applying energy to the lesion, e.g. an ultrasonic means; and visualization or monitoring means; etc.

All of the above components are conveniently present in a catheter device capable of accessing the cardiovascular site of interest. The catheter device is capable of operatively communicating with other components and devices necessary for operation of the catheter, such as fluid flow means, fluid reservoirs, power means, pressurized gas supply means, and the like, as described below, that are part of the overall system employed to practice the subject methods.

Representative Devices for Use in Practicing the Subject Methods

Representative embodiments of dissolution fluid introduction (and in certain embodiments removal) means are now described in greater detail in terms of the figures. FIG. 1 provides a representation of a device for use in practicing the invention. Artery 12 (shown in cutaway view) has calcified lesion 14 on its inner surface 16. Catheter 11 is positioned proximal to the target lesion 14. At the distal end of catheter 11 is opening 13 which provides for flow of dissolution fluid from the catheter into the local environment of the lesion and opening 15 which provides for flow of fluid from the local environment of the lesion into the catheter and out of the patient. Catheter 11 also includes balloon element 17 which is inflated to render the local environment of the lesion substantially bloodless. During use, fluid inflow and outflow are kept at substantially equal rates so as to maintain a substantially constant pressure in the region of the target lesion. In certain embodiments, the catheter is configured such that dissolution fluid is forced out of port 13 at high pressure (e.g. as a jet). This embodiment finds particular use in the treatment of occlusive lesions, as described in greater detail infra. See FIG. 5.

Figure 2:
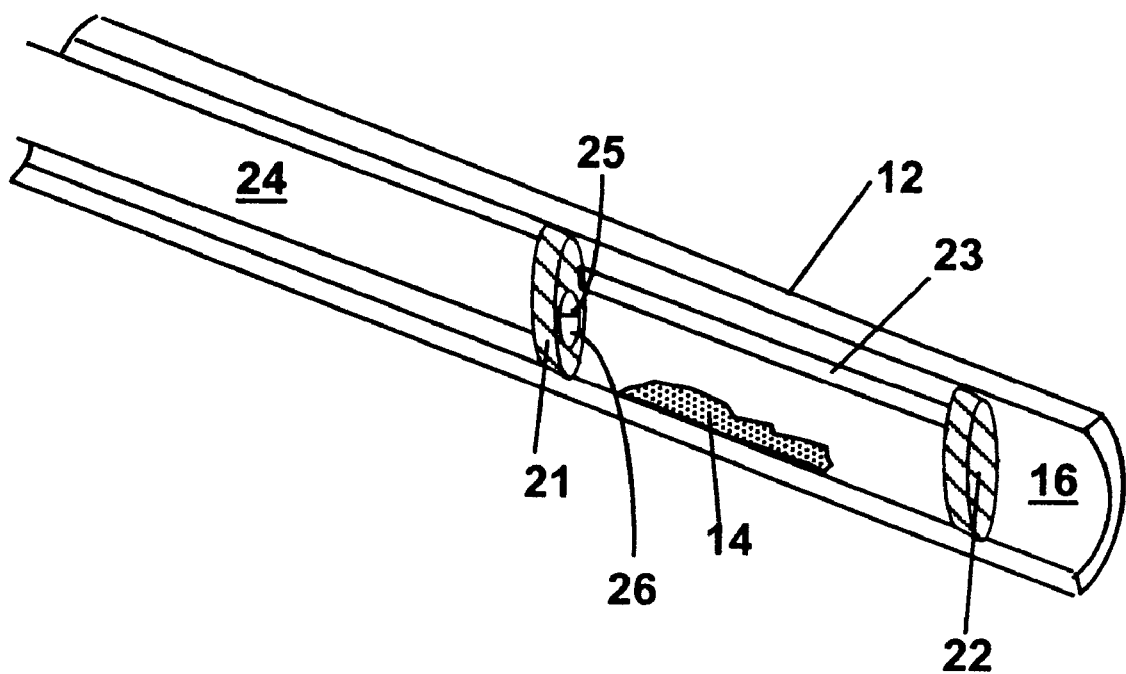
FIG. 2 provides a cutaway view of a vessel being treated according to a second embodiment of the subject invention.

FIG. 2 provides a representation of another catheter design that can be employed to practice the subject methods. In FIG. 2, catheter 24 has two inflatable balloons 21 and 22 connected by a conduit 23 at its distal end. Catheter 24 also has fluid inflow opening 25 and fluid outflow opening 26 for introducing and removing dissolution fluid from the local environment of the target lesion 14. During use, the catheter is inserted and the balloons inflated such that the local environment of the target lesion becomes substantially sealed from the remainder of the host's circulatory system. The local environment is then flushed with dissolution fluid using openings 25 and 26.

Figure 3:
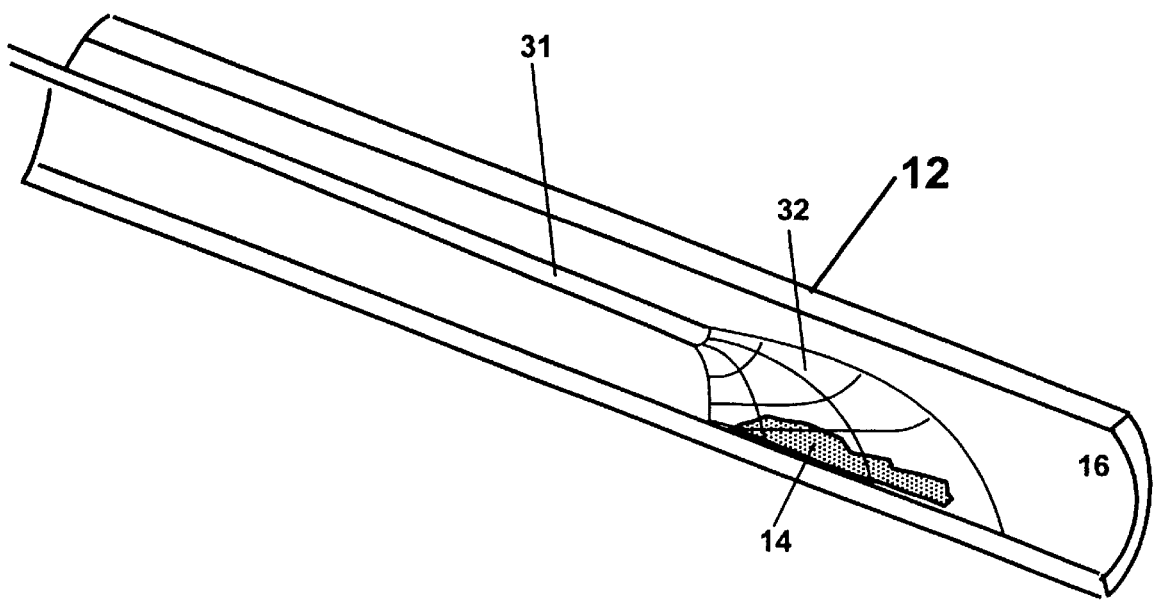
FIG. 3 provides a cutaway view of a vessel being treated according to a third embodiment of the subject invention.

FIG. 3 provides a representation of yet another catheter device that has been designed for use in connection with the present invention. The device is designed for use in minimally invasive procedures and in an open surgical field. The catheter is shown in artery 12 having calcified target lesion 14. Catheter 31 has a flexible cup 32 secured near the distal end of the catheter (shown in transparent lines). In one embodiment, the cup can be folded for insertion into the vessel, and then expanded at the desired location in the vicinity of the mineralized area. A defined area or local environment is created by the contact of the cup 32 with the vessel wall 16. The catheter is designed to allow infusion of the local environment with the dissolution solution. The catheter is composed of flexible tubing such that it can be situated at any position along a vessel, and should be sufficiently strong so that it withstands the pressure created from the both the flow of the acidic treatment solution and the suction generated during the removal of the acidic treatment solution. Cup 32 can be held in place by maintaining the pressure within the local environment sufficiently below blood pressure, or optionally by a balloon (not shown) or other means. An ultrasound probe (not shown) may be used to generate ultrasonic energy.

In one embodiment, the catheter 31 is a single lumen catheter. The lumen of the catheter communicates with the interior of the flexible cup 32. A dissolution solution can be applied through the catheter to the local environment for the desired time period. Following this time period, the cup is removed, and the dissolution solution is allowed to disperse. Alternatively, a device to create suction can be applied to the more proximal end of the catheter so that the dissolution solution is drawn away from the defined area via the single lumen. Similarly, following treatment with the dissolution solution the rinsing agent can be applied through the single-lumen catheter, if desired.

In another embodiment, the catheter 31 is a double-lumen catheter, both of which communicate with the interior of the flexible cup 32. One of the lumens allows the infusion of either the dissolution solution or a rinsing solution. The second lumen removes the dissolution or rinse solution. Infusion and suction can be alternated, or the two process can be applied simultaneously to create a flow of solution.

In yet another embodiment, catheter 31 is a triple-lumen catheter, all of which communicate with the interior of flexible cup 32. In this embodiment, one of the lumens allows the infusion of the dissolution solution, one of the lumens allows the infusion of a rinsing solution, and one of the lumens allow for the application of suction for the removal of solution.

Figure 4:
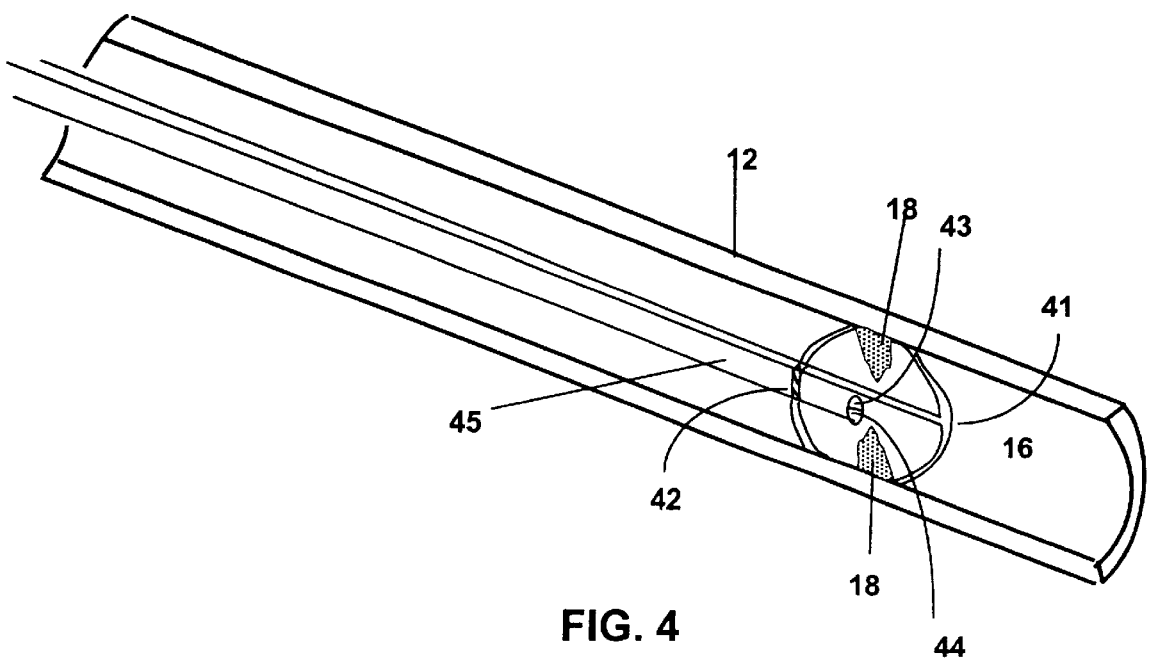
FIG. 4 provides a cutaway view of a vessel being treated according to a fourth embodiment of the subject invention.

Referring to FIG. 4, a double cup assembly for use with the present invention is shown. The assembly is designed for use in minimally invasive procedures and in an open surgical field. In this apparatus, catheter 45 includes first and second expandable cups 41 and 42. The cups can be placed on either side of a calcified target lesion, such as a calcified valve 18 shown in FIG. 4. This first cup 42 is placed in close proximity to one side of valve 18. One lumen of the catheter passes through the opening of the valve 18, as is terminates at second cup 41, which is placed in close proximity to the opposite side of the valve. Catheter 45 also include fluid introduction 43 and fluid extraction 44 openings for introducing and removing fluid from the local environment bounded by the cups 41 and 42.

Additional catheter devices that may be employed to practice the subject methods include those described in U.S. Pat. Nos. 4,610,662; 4,573,966; 4,636,195; 4,824,436; 5,059,178; 5,090,960; 5,167,628; and 5,222,941; the disclosures of which are herein incorporated by reference.

Additional Method Steps

In a number of embodiments of the subject methods, the above step of maintaining the local environment of the lesion at a subphysiological pH for a sufficient period of time for demineralization of the target calcified lesion to occur is used in conjunction with one or more additional method steps in order to achieve the overall mineral reduction in the target lesion. Additional methods steps that may be present in the overall process include: rendering the region of the target lesion bloodless, contacting the target lesion with a solution designed to remove organic components, washing or rinsing the local environment of the target lesion, contacting the treated vascular site with one or more active agents, and the like.

Where one or more additional distinct solutions, such as priming solutions, washing solutions, organic phase dissolution solutions and the like are employed, as described below, such disparate solutions are generally introduced sequentially to the site of the target lesion. For example, the target lesion may be contacted with the following order of solutions: (1) priming solution to render the local environment substantially bloodless; (2) organic phase dissolution solution, e.g. detergent solution such as cholic acid solution, to remove organic phases from the target lesion; (3) acidic dissolution solution to demineralize the target lesion; and (4) washing solution. Other sequences of solution application can also be employed.

Rendering the Region of the Target Lesion Bloodless

In many preferred embodiments, as described above, the local environment of the lesion is rendered substantially bloodless prior to introduction of the dissolution fluid. In these embodiments, the local environment may be rendered substantially bloodless using a variety of different protocols. Typically, a priming solution will be employed in this step of rendering the local environment bloodless. Examples of priming solutions that may find use in these embodiments include: water for injection, saline solutions, e.g. Ringer's, or other physiologically acceptable solutions. The priming solution includes an anticlotting factor in many embodiments, where anticlotting factors of interest include heparin and the like. The priming solution can also contain chelating agents.

Removal of blood from the local environment with the priming solution can be accomplished using any convenient protocol. For example, where cannulation is employed, e.g. to isolate a stretch of a blood vessel or to isolate a limbic extremity, the local environment of the lesion may be flushed with a washing solution by introducing fluid through the proximal (upstream) cannula and removing blood from the downstream (distal) cannula. Where the device that is employed to introduce the dissolution fluid further includes a means for substantially isolating the local environment of the lesion (e.g. a balloon or a cup as described above), the contacting step of the subject methods further comprises a step of substantially isolating the local environment of the lesion from the remainder of the subject's circulatory system. This isolation step varies depending on the particular nature of the device employed. Thus, in certain embodiments, isolation includes inflating balloons at either end of the lesion, thereby substantially isolating the local environment of the lesion.

Use of Organic Structure Dissolution Solutions

As mentioned above, in addition to the acidic dissolution solution, certain embodiments of the subject invention include a step of contacting the target lesion with a dissolution solution which serves to remove at least a portion of the non-mineral, typically organic, phase of the target lesion. The nature of this "organic phase dissolution solution" varies depending on the nature of the target lesion. Representative active agents that may be present in this organic phase dissolution solution include: oxidizing agents; organic solvents; lipid dissolving agents such as surfactants, e.g. TWEEN™, and detergents, where ionic detergents are of particular interest, e.g. cholic acid, glycocholic acid, benzylkonium chloride; enzymes, and the like.

Basic Solutions

In one embodiment, the priming solution is a basic solution. The basic solution can be composed of any inorganic or organic base. The basic solution can be a concentrated base, or can be a dilute basic solution. The pH of the basic solution is generally greater than about 9.0. In one embodiment, the basic solution has a pH between about 10.0 and about 12.0. The basic solution can be a solution of an inorganic base. In one embodiment, the basic solution is a solution of sodium hydroxide (NaOH). In one embodiment, the basic solution is a dilute solution of sodium hypochlorite.

Washing

In most embodiments, it is desirable to rinse or wash the local environment of the lesion following treatment with the dissolution solution. The rinsing solution can be any solution sufficient to remove or dilute the acidic treatment solution from the vascular tissue, thereby reducing the acidity in the local environment of the lesion. In one embodiment, the rinsing solution is a neutral solution. The solution may include an anticlotting factor, such as heparin. The neutral rinsing solution can be a buffered solution of physiological pH. Preferably, the neutral rinsing solution has a pH of about 7.0 to about 8.0. More preferably, the neutral rinsing solution has a pH of about 7.4. One non-limiting example of a neutral rinsing solution is phosphate buffered saline.

Lesion Inhibition Agents

In certain embodiments, it is of interest to further treat the local environment of the lesion, i.e. which may or may not comprise any of the originally present lesions, depending on the particular method conducted, with one or more agents that serve to inhibit the formation of the new calcified lesion on the vascular tissue on which the lesion was present. Inhibition agents that may be employed include: water-soluble phosphate esters (e.g., sodium dodecyl hydrogen phosphate, as described in U.S. Pat. No. 4,402,697, the disclosure of which is herein incorporated by reference); water soluble quaternary ammonium salts (e.g., dodecyltrimethyammonium chloride, as described in U.S. Pat. No. 4,405,327, the disclosure of which is herein incorporated by reference); sulfated higher aliphatic alcohols (e.g., sodium dodecyl sulfate, as described in U.S. Pat. No. 4,323,358, the disclosure of which is herein incorporated by reference); agents that result in the covalent coupling of aliphatic carboxylic acids (as described in U.S. Pat. No. 4,976,733, the disclosure of which is herein incorporated by reference); and the like. Other agents of interest that may be employed including agents of biological origin, such as growth factor inhibitors, angiogenisis inhibitors and the like.

In certain embodiments, the local environment of the lesion is contacted with a wound healing or growth promoting solution that provides various growth factors to the local environment of the lesion to promote healing of the site. Growth factors of interest include: platelet derived growth factor, keratinocyte growth factor, basic fibroblast growth factor, leukocyte derived growth factor-2 (LDGF-2), transforming growth factor, epidermal growth factor (EGF), connective tissue growth factor, fibroblast growth factor 11, vascular IBP-like growth factor, epithelial cells growth factor, fibroblast growth factor 13, insulin-like growth factor-1, vascular endothelial growth factor (VEG-F), and the like.

Application of External Energy

In certain embodiments, external energy is applied to the target lesion to promote mechanical break-up of the lesion into particles or debris that can be easily removed from the site of the lesion. Any means of applying external energy to the lesion may be employed. As such, jets or other such means on a catheter device which are capable of providing varying external forces to the lesion sufficient to cause the lesion to break up or disrupt may be employed. Of particular interest in many embodiments is the use of ultrasound. The ultrasound can be applied during the entire time of contact of the cardiovascular tissue with the acidic treatment solution, or the ultrasound can be applied for only part of the treatment period. In one embodiment, ultrasound is applied for several short periods of time while the dissolution treatment solution is contacted with the cardiovascular tissue. There are several devices for the application of ultrasound to cardiovascular tissue known to those of skill in the art. For example, U.S. Pat. No. 4,808,153, the disclosure of which is herein incorporated by reference, describes an ultrasound apparatus to be used in an artery without damaging the artery, and U.S. Pat. No. 5,432,663, the disclosure of which is herein incorporated by reference, describes an apparatus for generating ultrasonic energy useful for removal of intravascular blockages. The ultrasound can be low frequency ultrasound.

In such methods where external energy is applied to the lesion in order to disrupt or break-up the lesion into particles or debris, the particles or debris may range in size from about 0.01 to 4.0 mm, usually from about 0.1 to 2.0 mm and more usually from about 0.5 to 1.0 mm. In such instances, the method may further include a step in which the resultant particles are removed from the local environment of the lesion. Particles may be removed from the local environment of the lesion using any convenient means, such as the catheter of the subject invention described in greater detail infra.

Another means that may be employed to apply external energy to the lesion during the dissolution process is to use a mechanical means of applying external energy. Mechanical means of interest include moving structures, e.g. rotating wires, which physically contact the target lesion and thereby apply physical external energy to the target lesion.

Imaging

In addition, it may be convenient to monitor or visualize the lesion prior to or during treatment. A variety of suitable monitoring means are known to those of skill in the art. Any convenient means of invasive or noninvasive detection and/or quantification may be employed. Such means include plain film roentgenography, coronary arteriography, fluoroscopy, including digital subtraction fluoroscopy, cinefluorography, conventional, helical and electron beam computed tomography, intravascular ultrasound (IVUS), magnetic resonance imaging, transthoracic and transesophageal echocardiography, rapid CT scanning, antioscopy and the like. Any of these means can be used to monitor the reduction in mineralization by the method of the invention.

Demineralization of Calcified Lesions

Maintenance of the local environment of the calcified lesion at a subphysiologic pH, as described above, results in at least partial demineralization of the lesion, i.e. at least a reduction of the calcium phosphate content of the lesion. By reduction is meant that the total overall dry weight of calcium phosphate mineral is reduced or decreased, generally by at least about 50%, usually by at least about 75% and more usually by at least about 90%. In certain embodiments, substantially all of the calcium phosphate content of the lesion may be removed, where by substantially all is meant at least about 90%, usually at least about 95% and preferably at least about 99% dry weight of the original calcium phosphate present in the lesion is removed.

Utility

The subject methods find use in a variety of different applications in which it is desired to at least reduce, if not substantially remove, at least the mineral component of a calcified lesion. One application in which the subject methods find use is in the treatment of a host suffering from a vascular disease associated with the presence of vascular calcified lesions. Such vascular diseases include diseases in which one or more different calcified lesions are present on one or more locations of the vascular tissue of the host, where the lesion(s) may be present on a vessel wall, on a valve, etc.

By treatment is meant at least a reduction in a parameter of the disease, where parameter may include typical symptoms indicative of occluded vessels or malfunctioning valves, e.g. chest pains, angina, limb ischemia, etc., or risk factors associated with the disease or condition, e.g. narrowing of arteries, and the like. Treatment also includes situations where the host is cured of the vascular disease, i.e. where the lesion is completely removed.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the hosts will be humans.

The subject inventions finds use in a number of specific representative applications. These applications include: peripheral demineralizing atherectomies; coronary demineralizing atherectomies; and valve/annular demineralizations. Each of these applications is discussed in greater detail separately below.

Peripheral Demineralizing Atherectomy

One type of specific method provided by the subject invention is a peripheral demineralizing atherectomy, in which a calcified target lesion present in a peripheral vessel, e.g. artery or vein, of the circulatory system is demineralized. The target lesion may be present in any peripheral vessel, where the subject methods are particularly suited for use in the demineralization of lesions that are present in the renal, iliac, femoral, arteries, arteries of the lower extremities, and A-V access sites.

In peripheral demineralizing atherectomy procedures according to the subject invention, the target calcified lesion is typically flushed with a dissolution solution according to the subject invention for a sufficient period of time for the desired demineralization of the target lesion to occur. The manner in which the target lesion is flushed with the solution generally depends on the nature of the device that is employed, as well as the nature of the target lesion. For example, one may cannulate the vessel on either side of the lesion, with the upstream cannula being used to introduce the dissolution solution and the downstream cannula being used to remove solution from the vessel. In these embodiments, isolation of the limb comprising the target peripheral vessel may be indicated, as described above.

Figure 5:
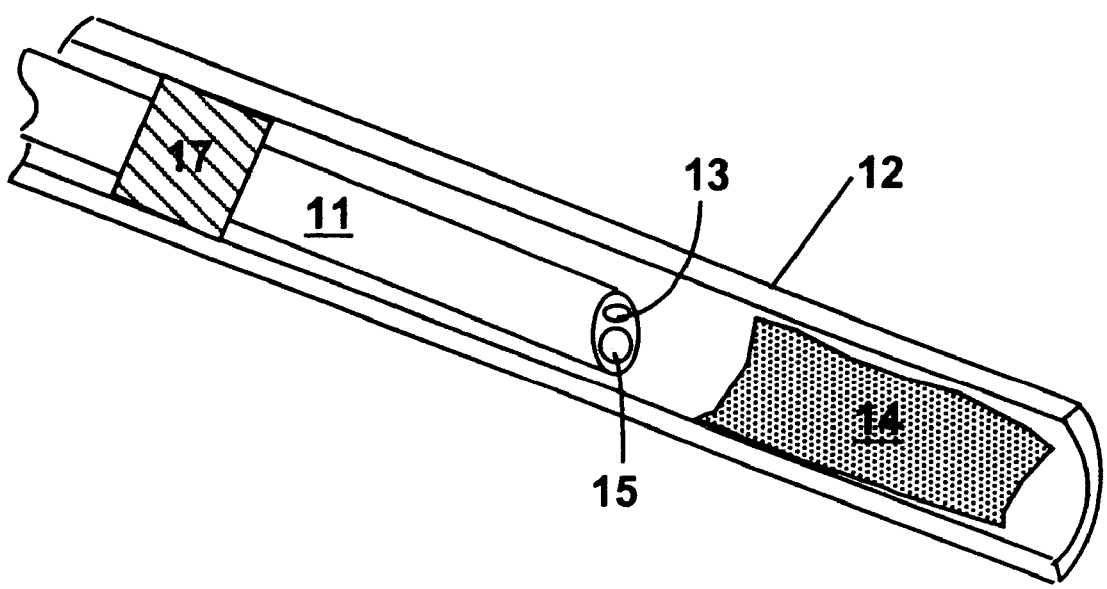
FIG. 5 provides a cutaway view of a vessel being treated according to a fifth embodiment of the subject invention, in which the target lesion totally occludes the host vessel.

Alternatively, a catheter device that provides for a substantially sealed local environment of the target lesion may be employed to introduce and remove the dissolution solution from the site of the target lesion. These procedures are particularly suited for the treatment of calcified target lesions that do not substantially occlude the peripheral vessel. Where the vessel is substantially, if not completely, occluded by the target lesion, a device as shown in FIG. 5 may be employed. In FIG. 5, catheter 11 has outlet 13 and inlet 15 and is positioned next to the upstream side of the target lesion 14 that substantially completely occludes the vessel 12. Dissolution fluid is contacted with the target lesion 14 by flowing the dissolution fluid out of the opening 13, preferably under pressure such that the target lesion is contacted with a "jet" of dissolution fluid. Fluid is also removed via port 15. Importantly, the rate of inflow and outflow of fluid from the site of the target lesion is kept substantially constant so that pressure is not substantially elevated at the site of the target lesion. This process results in a steady decrease in the size of the target lesion, at least to a point where the lesion does not substantially completely occlude the target vessel.

The above procedure may be used by itself in a given treatment process, where demineralization of the target lesion is sufficient to achieve the desired outcome of the particular therapy indicated by the host's condition. Alternatively, the above procedure may be used in combination with additional treatment modalities, including balloon angioplasty; stenting; mechanical atherectomy; bypass and the like, where the subject method of performing a peripheral demineralizing atherectomy serves to prepare the target lesion and vessel for the subsequent treatment. Thus, the subject methods find use in: facilitating the placement of balloon catheters in narrow, focal, calcified lesions; facilitating the placement of stents in narrow, focal, calcified lesions; treating total peripheral vascular occlusions; and facilitating surgical bypass by removing calcification at proximal and/or distal anastomotic sites or converting procedures to percutaneous procedures.

Coronary Demineralizing Atherectomy

Another type of specific method provided by the subject invention is a coronary demineralizing atherectomy, in which a calcified target lesion present in a vessel associated with the heart, e.g. coronary artery, is demineralized. The target lesion may be present in any coronary vessel, such as the aorta, coronary arteries, etc.

In coronary demineralizing atherectomy procedures according to the subject invention, the target calcified lesion is typically flushed with a dissolution solution according to the subject invention for a sufficient period of time for the desired demineralization of the target lesion to occur. The manner in which the target lesion is flushed with the solution generally depends on the nature of the device that is employed, as well as the nature of the target lesion. For example, where the coronary vessel is not totally occluded by the target lesion, a catheter device that provides for a substantially sealed local environment of the target lesion may be employed to introduce and remove the dissolution solution from the site of the target lesion. See e.g. FIG. 2. Where the vessel is substantially, if not completely, occluded by the target lesion, a device as shown in FIG. 5 may be employed. In FIG. 5, catheter 11 has outlet 13 and inlet 15 and is positioned next to the upstream side of the coronary target lesion 14 that substantially completely occludes the coronary vessel 12. Dissolution fluid is contacted with the target lesion 14 by flowing the dissolution fluid out of the opening 13, preferably under pressure as described above.

Fluid is also removed via port 15. Importantly, the rate of inflow and outflow of fluid from the site of the target lesion is kept substantially constant so that pressure is not substantially elevated at the site of the target lesion. This process results in a steady decrease in the size of the target lesion, at least to a point where the lesion does not substantially completely occlude the target vessel.

The above procedure may be used by itself in a given treatment process, where demineralization of the target lesion is sufficient to achieve the desired outcome of the particular therapy indicated by the host's condition. Alternatively, the above procedure may be used in combination with additional treatment modalities, including balloon angioplasty; stenting; mechanical atherectomy; coronary artery bypass and the like, where the subject method of performing a coronary demineralizing atherectomy serves to prepare the target lesion and vessel for the subsequent treatment. Thus, the subject methods find use in: facilitating the placement of balloon catheters in narrow, focal, calcified lesions of coronary vessels; facilitating the placement of stents in narrow, focal, calcified lesions of coronary vessels; treating total peripheral vascular occlusions in coronary vesels; and facilitating coronary vessel surgical bypass by removing calcification in proximal and/or distal anastomotic sites or converting procedures to percutaneous procedures.

Valve/Annulus Demineralization

Yet another application in which the subject methods find use is in the demineralization of valves and/or annuli, typically those found in the heart or vessels closely associated therewith, e.g. the aortic valve, mitral annuli, etc. In other words, the subject methods are useful in demineralizing valvuloplasties or annuloplasties. The valve/annular structure that is treatable according to the subject methods may be endogenous to the host or bioprosthetic, i.e. an implant, where the implant may be a allogenic, xenogeneic, synthetic, etc.

In demineralizing a valve/annular structure according to this particular application of the subject invention, the valve or structure having the calcified lesion present thereon is typically flushed with a dissolution solution, as described above. In many embodiments, the local environment of the valve/annular structure is substantially isolated from the remainder of the host's circulatory system during this flushing step. A variety of different devices may be employed to flush the structure with the dissolution solution, including that shown in FIG. 4 described supra, that disclosed in U.S. Pat. No. 5,167,628 the disclosure of which is herein incorporated by reference, and the like.

Demineralizing valvuloplasties and annuloplasties according to the subject invention can be used to achieve a number of different therapeutic goals, including: (a) extension of the useful live of bioprosthetic implants; (b) enhancing the efficacy of annuloplasty ring placement; (c) decreasing the calcification of native heart valves, thereby delaying valve replacement; and the like.

Systems

Also provided by the subject invention are systems for use in performing the subject methods. The systems of the subject invention include at least a dissolution fluid introductions means, such as the subject catheters described above, and a dissolution fluid reservoir capable holding or storing the dissolution fluid just prior to administration to the local environment of the lesion. In addition, the subject systems will typically include a means for moving the dissolution fluid through the fluid introduction means to the local environment of the lesion, where such means is typically a pump, large syringe, and the like. The system may also conveniently include a means for maintaining the pressure and/or temperature of the dissolution fluid at a desired value. In addition, the subject systems typically include a means for removing fluid from the local environment of the lesion, e.g. a second pumping means or suction means. The above elements of the subject system may conveniently be present in housing fabricated of a suitable material.

Kits

Also provided are kits for use in performing the subject methods. The kits typically comprise at least the dissolution fluid to be used in the subject methods, such as a hydrochloric acid solution or carbonic acid solution, as described above, where the solution may be present in a pressurized and/or climate controlled container so as to preserve the stability of the dissolution solution. For kits that are to be used in methodologies in which the fluid is flushed through the local environment of the lesion, the amount of dissolution fluid present in the kit ranges from about 1 to 500 liters, usually from about 10 to 200 liters and more usually from about 50 to 100 liters. For kits that are to be used in static methodologies, the amount of dissolution fluid present in the kit generally ranges from about 100 ml to 1 liter and usually from about 100 ml to 500 ml. Alternatively, the kit may comprise precursors of the dissolution solution for use in preparing the solution at the time of use. For example, the precursors may be provided in dry form for mixing with a fluid, e.g. water, at the time of use. Also present in the kit may be a fluid introduction (and even removal) means, as described supra. In addition to the dissolution fluid or precursors thereof, the kit may further comprise one or more additional fluids (or dry precursors thereof), such as a priming solution, a washing solution, and the like. Finally, the kits will include instructions for practicing the subject methods, where such instructions may be present on one or more of the kit components, the kit packaging and/or a kit package insert.

The following examples are offered by way of illustration and not by way of limitation.

Experimental

I. Analysis of Aortic Valve Mineralization

Two human aortic heart valves were removed during routine valve replacement therapy. These valves were dissected to separate mineralized deposits on the valve leaflets. The deposits where strongly adherent to the valve tissue and were incorporated into the structure of the leaflets as nodules. Both valves had extensive mineralize nodule formation. The nodules were hard and could not be fractured by hand. Contact x-rays were taken to document the extent and distribution of the mineralized nodules in the valve tissue. The mineralized areas demonstrated a radioopacy similar to well mineralized bone.

X-ray diffraction and Fourier Transform Infra Red Spectroscopy (FTIR) were performed using standard procedures (see Constantz, B. R., et al. 1995, Science 267: 1796–1799, herein incorporated by reference) on the removed samples, both directly and following removal of most organic material with sodium hypochlorite (CLOROX bleach). The XRD pattern of the mineralized tissue, both with and without the organics removed, showed the characteristic peaks of apatite. The reflections were poorly crystalline in nature, indicating small crystal size and low levels of crystalline order. The FTIR spectrogram of the mineralized tissue, both with and without the organics removed, further identify the mineralized deposit as apatite that contains substantial carbonate, termed a carbonated apatite (mineral name, dahllite).

Samples were prepared for scanning electron microscopy, using the methods of Constantz, B. R., 1986 (In: *Reef Diagenesis*, Schroeder, J., and Puser, B., (eds.), Springer-Verlag). The size of the crystals composing the mineralized deposit were less than one micron across. The solubility of the crystals in this size range is expected to modify by an order of magnitude due to their increased surface are to volume ratio (see Constantz, B. R., et al., 1986, supra).

The composition of the "calcific deposits" are not calcium or hydroxyapatite as commonly published, rather they are a carbonated apatite, dahllite, which is expected to be considerably more soluble than hydroxyapatite. Also the size and crystallinity of the crystals of dahllite comprising these deposits are that of very small, high surface area to volume ratio crystallites whose diffraction patterns indicate a very low degree of crystalline order, further increasing their solubility.

II. Mineral Dissolution Assays

A. Norian SRS® cement (obtained from Norian Corporation, Cupertino, Calif.) is prepared according to the manufacturer's instructions. The resultant paste is placed into Teflon mold rings and allowed to set to produce dahllite disks. The disks are then contacted with the following solutions: 0.1 M HCl, 1.0 M HCl, concentrated HCl 0.1 M HCl +0.01 M EDTA, 1.0 M HCl +0.01 M EDTA, concentrated HCl +0.1 M EDTA, 0.1 M $H_2SO_4$, 1.0 M $H_2SO_4$, 0.1 M $H_2SO_4$+0.01 M EDTA, 1.0 M $H_2SO_4$+0.1 M EDTA, 1.0 M formic acid, concentrated fromic acid, 1.0 M formic acid +0.1 M EDTA, 1.0 M acetic acid, concentrated acetic acid, 1.0 M acetic acid and 0.1 M EDTA, 1.0 M succinic acid, 1.0 M succinic acid +0.1 M EDTA; 0.1 M carbonic acid; and 1.0 M carbonic acid. A dissolution graph is then prepared for each solution which plots $Ca^{2+}$ concentration over time. By comparing the different dissolution graphs, the solubility of dahllite in different dissolution solutions is compared.

B. Dissolution of Bolus of Dahllite in 0.05N HCl with Various Ionic Strengths Using Pump at 69 ml/min.

1. Introduction

Six dissolution experiments were conducted to determine the affect of ionic strength on the dissolution rate of carbonated hydroxyapatite in HCl. According to the Kinetic Salt Effect theory, oppositely charged ions react more slowly as the ionic strength of the solution is increased because the electrostatic attraction between the reacting ions is decreased. The object of this experiment was to determine if the theory holds for the dissolution reaction of carbonated hydroxyapatite with HCl.

2. Experimental

A Cole-Parmer peristaltic pump (model #7520–35) was used to deliver the demineralizing 0.05N HCl solution with varying NaCl concentrations to the sample of carbonated hydroxyapatite (i.e. dahllite), $Ca_{8.8}(HPO_4)_{0.7}(PO_4)_{4.5}(CO_3)_{0.7}(OH)_{1.3}$, in the form of a spherical bolus. In each case, a 100±3 mg bolus (dry weight) of carbonated hydroxyapatite was soaked in deionized water until there was no further weight gain. This weight was taken to be the initial weight of the bolus. The bolus was then transferred to a 12 ml disposable liquid transfer pipette and a peristaltic pump with a rubber stopper on one end of the tubing was attached. Solutions were pumped through the pipette past the bolus at a rate of approximately 69 ml/min in 5 minute time intervals and the weight of the bolus was measured at the end of each interval. The dissolution process was continued until the weight of the bolus was less than 5 mg. The NaCl concentrations used were: 0, 5.8 (isotonic), 11.6, and 25 g/L.

3. Results

The results of the six dissolution experiments are tabulated below. A table of the respective half-lives follows. The wet weight of the bolus at t=0 is represented by m(o), and m(t) is the weight at a given time interval (m=mass).

TABLE 1

Dissolution of Bolus of 0.05N HCl with Various Ionic Strengths

| Time (min) | log[m(t)/m(0)] | | | | | |
|---|---|---|---|---|---|---|
| | No salt | No salt(2) | 5.8 g NaCl | 5.8 g NaCl(2) | 11.6 g NaCl | 25 g NaCl |
| 0.0 | 0.0000 | 0.0000 | 0.0000 | 0.0000 | 0.0000 | 0.0000 |
| 5.0 | −0.0569 | −0.0982 | −0.0789 | −0.0822 | −0.1209 | −0.1300 |
| 10.0 | −0.1374 | −0.2121 | −0.1926 | −0.1803 | −0.2287 | −0.3014 |
| 15.0 | −0.2403 | −0.3212 | −0.3322 | −0.2906 | −0.3973 | −0.5792 |
| 20.0 | −0.3594 | −0.4491 | −0.5195 | −0.4514 | −0.6717 | |
| 25.0 | −0.4765 | −0.5907 | −0.8683 | −0.6736 | | |
| 30.0 | −0.6273 | −0.7788 | | −1.2653 | | |
| 35.0 | −0.8154 | −1.0740 | | | | |

Half-lives for the Dissolution of Bolus in 0.05N HCl

| Half-life (min) | No Salt | No Salt (2) | 5.8 g NaCl | 5.8 g NaCl (2) | 11.6 g NaCl | 25 g NaCl |
|---|---|---|---|---|---|---|
| | 15.8 | 12.7 | 11.6 | 11.8 | 10.5 | 8.8 |

4. Discussion and Conclusion

The half-life data and log[m(t)/m(0)] vs. time show that increasing the ionic strength of the solution increases the dissolution rate. This contradicts the Kinetic Salt Effect theory which says that increasing the ionic strength of a solution decreases the reaction rate between oppositely charged ions due to a decrease in electrostatic attraction between the ions. In this case, $Na^+$ and $Cl^-$ ions should theoretically decrease the electrostatic attraction between $H^+$ and both $HPO_4^{2-}$ and $PO_4^{3-}$ and slow the rate of dissolution.

C. Dissolution of Bolus in HCl Solutions of Various pH

1. Introduction

Eight sets of dissolution experiments were conducted to determine the affect of pH on the dissolution rate of carbonated hydroxyapatite in HCl. It was predicted that a decrease in pH (increase in $H^+$) should increase the rate of dissolution. In addition, three different methods of dissolution were used to see how altering the method would affect the dissolution rate.

2. Experimental

For each experiment, a 100+3 mg (dry weight) sample of carbonated hydroxyapatite, $Ca_{8.8}(HPO_4)_{0.7}(PO_4)_{4.5}(CO_3)_{0.7}(OH)_{1.3}$, in the form of a spherical bolus was used. The bolus was soaked in deionized water until there was no further weight gain and this weight was taken to be the initial weight of the bolus. Descriptions of the three dissolution methods are below. For each set of experiments, nine pH levels were studied.

i. Stirring

For the stirring experiments, the bolus was placed in a beaker with a volume of HCl solution that provided twice the stoichiometric number of protons necessary to dissolve the carbonated hydroxyapatite. A stir bar of appropriate size was added to the beaker and the solution was stirred on an IKA Labortechnik stir plate on a setting of 6. For each experiment, the weight of the bolus was measured at time intervals appropriate for the pH of the solution used until the weight of the bolus was less than 5 mg. pK was calculated from the slope of the linear regression line for each set of data points using the following formula:

$$pK = -\log[1.533 * \text{slope}]$$

ii. Sonication

Sonication experiments employed a Branson Sonifier 450 to deliver ultrasound to the HCl solution. Power outputs of 9 Watts, 35 Watts, and 53 Watts were used. The solutions were also stirred on an IKA Colorsquid stir plate on a setting of 2 to ensure complete mixing. The bolus was placed in a beaker with a volume of HCl solution that provided twice the stoichiometric number of protons necessary to dissolve the it, and weight measurements were made at time intervals appropriate for the pH of the solution until the weight was less than 5 mg. pK was calculated as it was for the stirring experiments.

iii. Pump

A Cole-Parmer peristaltic pump (model #7520–35) was used to deliver the HCl solution to bolus. The bolus was placed in a 12 ml disposable liquid transfer pipette and the peristaltic pump with a rubber stopper on one end of the tubing was attached. Solutions were pumped through the pipette past the bolus at rates of approximately 16 ml/min, 33 ml/min, 69 ml/min, and 110 ml/min. Weight measurements were made at appropriate time intervals until the weight was less than 5 mg, and pK was calculated as before.

3. Results

The results of the eight sets of dissolution experiments are included in Table 2 below. Graphs were also generated from the observed data. Rate measurements for 0.8N, 0.6N and 0.075N were not taken for the sonication and pump experiments because the slope of the pK vs. pH linear regression line for the stirring experiment was relatively unchanged by including these points. Note that a lower pK indicates a faster dissolution rate.

observed. Increasing the ultrasonic power may help dissolution by either increasing the surface area due to these craters, increasing the mixing of the solution, or both. It may also dislodge particles from the surface of the bolus that are not yet dissolved.

Of the three dissolution methods studied, the pump gave the fastest dissolution rate. The rate consistently increased as the pump flow rate was increased. The maximum flow rate for the peristaltic pump that was used was 110 ml/min, but it is anticipated that a faster dissolution rate may be achieved by using a faster pump. The faster rate may be attributed to the fact that a larger volume of solution (more than double the stoichiometric number of protons) must be used with the pump, and that the bolus is always exposed to fresh solution which is equivalent to ultimate mixing. The stream of solution may also mechanically remove particles from the bolus.

One final observation from the pK vs. pH graph is that differences in rate for the different methods decrease as pH decreases. In other words, rates vary less at pH 0 and vary more at pH 2. Therefore, for solutions of higher proton concentration, the rate of dissolution is less dependent on the method employed.

D. Dissolution of Bolus in HCl Solutions using Ultrasound

1. Introduction.

Six sets of dissolution experiments were conducted to determine the effect of Ultrasound on the dissolution rate of carbonated hydroxyapatite in HCl. It was predicted that an increase in ultrasonic power should increase the rate of dissolution due to an increase in mixing of the solution.

TABLE 2 pKs Resulting from Dissolution of Bolus with Various HCl Solutions and Various Dissolution Methods

| HCl concentration (N) | pH | Stirring | Sonication 9W | Sonication 35W | Sonication 53W | Pump 16 ml/min | Pump 33 ml/min | Pump 69 ml/min | Pump 110 ml/min |
|---|---|---|---|---|---|---|---|---|---|
| 1.000 | 0.000 | 0.7189 | 0.1997 | 0.2634 | 0.3557 | 0.4190 | 0.2710 | 0.2392 | 0.2069 |
| 0.800 | 0.097 | 0.8204 | | | | | | | |
| 0.600 | 0.222 | 1.1122 | | | | | | | |
| 0.400 | 0.398 | 1.2840 | 0.7086 | 0.5689 | 0.6252 | 0.8400 | 0.5717 | 0.4875 | 0.4195 |
| 0.200 | 0.699 | 1.6950 | 0.9987 | 0.8799 | 0.6922 | 1.1140 | 0.9887 | 0.7103 | 0.7015 |
| 0.100 | 1.000 | 1.8600 | 1.4970 | 1.1693 | 1.1146 | 1.2390 | 1.1524 | 1.0674 | 0.8288 |
| 0.075 | 1.125 | 2.0310 | | | | | | | |
| 0.050 | 1.301 | 1.9440 | 1.9612 | 1.4658 | 1.5364 | 1.5020 | 1.4340 | 1.2938 | 0.9704 |
| 0.001 | 2.000 | 2.2440 | 2.3607 | 2.3773 | 2.0659 | 2.3240 | 1.9982 | 1.8080 | 1.6649 |

4. Discussion and Conclusion

Several conclusions may be drawn from the results of these experiments. First, the positive slopes of the lines on the pK vs. pH graph (not shown) show that a decrease in pH of the solution (increase in $H^+$) results in an increase in dissolution rate (decrease in pK) as expected. The dissolution involves $H^+$, $HPO_4^{2-}$ and $PO_4^{2-}$ ions, so it makes sense that increasing $H^+$ should increase the dissolution rate.

Both sonication and the pump gave faster dissolution rates than stirring alone. This is most likely due to the fact that sonication and pumping provide better mixing of the solution, effectively removing any layer of dissolved or reprecipitated material from the immediate area surrounding the bolus.

For the sonication experiments, increasing the ultrasonic power increased the rate of dissolution. When ultrasound was used, tiny craters in the surface of the bolus were 2. Experimental For each experiment, a 100±3 mg (dry weight) sample of carbonated hydroxyapatite, $Ca_{8.8}(HPO_4)_{0.7}(PO_4)_{4.5}(CO_3)_{0.7}(OH)_{1.3}$, in the form of a spherical bolus was used. The bolus was soaked in deionized water until there was no further weight gain and this weight was taken to be the initial weight of the bolus. The bolus was placed in a beaker with a volume of HCl solution that provided twice the stoichiometric number of protons necessary to dissolve it, and a Branson Sonifier 450 was employed to deliver ultrasound to the solution. Various HCl solutions were employed. The 0.1N, 0.05N, and 0.01N HCl solutions were made isotonic (300 mOsmol) with NaCl. Power outputs of 9 Watts, 35 Watts, and 53 Watts were used. The solutions were also stirred on an IKA Colorsquid stir plate on a setting of 2 to ensure complete mixing. Weight measurements were made at time intervals appropriate for the pH of the solution until the weight was less than 5 mg. pK was calculated from the slope of the linear regression line for each set of data points using the following formula:

$$pK = -\log[1.533 * \text{slope}]$$

3. Results

The results of the six sets of dissolution experiments are tabulated below in Table 3. Note that a lower pK indicates a faster dissolution rate.

TABLE 3

| Ultrasonic Power (Watts) | 1N HCl | 0.4N HCl | 0.2N HCl | 0.1N HCl | 0.05N HCl | 0.01N HCl |
|---|---|---|---|---|---|---|
| pKs Resulting from Dissolution of Bolus Using Ultrasound | | | | | | |
| 9 | 0.1997 | 0.7086 | 0.9987 | 1.497 | 1.9612 | 2.3607 |
| 35 | 0.2634 | 0.5689 | 0.8799 | 1.1693 | 1.4658 | 2.3773 |
| 53 | 0.3557 | 0.6252 | 0.6922 | 1.1146 | 1.5364 | 2.0659 |
| Half-lives (in min) Resulting from Dissolution of Bolus Using Ultrasound | | | | | | |
| 9 | 1.1 | 3.6 | 6.8 | 18.5 | 48.3 | 130.5 |
| 35 | 1.2 | 2.2 | 4.3 | 8.9 | 15.6 | 130.7 |
| 53 | 1.2 | 2.6 | 3 | 7.9 | 19.3 | 64.2 |

4. Discussion and Conclusion

The half-life data table shows that when the ultrasonic power was increased from 9 Watts to 35 Watts, the rate of dissolution increased for all solutions except 1N HCl and 0.01N HCl for which the rates remained relatively unchanged. The 1N HCl solution dissolves the bolus so quickly that any minor rate changes are difficult to observe. It is unclear why there was no observable increase in dissolution rate for the 0.01N solution. When the ultrasonic power was increased to 53 Watts, dissolution rates increased for all solutions except 1N and 0.4N, for which rates remained relatively unchanged, and 0.05N for which the rate decreased slightly. The results indicate that increasing the ultrasonic power increased the dissolution rate except when the rate is already so fast that minor changes are difficult to observe.

E. Dissolution of Bolus in HCl Solutions Using Pump

1. Introduction

Six sets of dissolution experiments were conducted to determine the effect of pump flow rate on the dissolution rate of carbonated hydroxyapatite in HCl. It was predicted that an increase in flow rate should increase the rate of dissolution due to an increase in exposure to protons.

2. Experimental

For each experiment, a 100±3 mg (dry weight) sample of carbonated hydroxyapatite, $Ca_{8.8}(HPO_4)_{0.7}(PO_4)_{4.5}(CO_3)_{0.7}(OH)_{1.3}$, in the form of a spherical bolus was used. The bolus was soaked in deionized water until there was no further weight gain and this weight was taken to be the initial weight of the bolus. The bolus was placed in a 12 ml disposable liquid transfer pipette and a Cole-Parmer peristaltic pump (model #7520-35) with a rubber stopper on one end of the tubing was attached. Various HCl solutions were pumped through the pipette past the bolus at rates of approximately 16 ml/min, 33 ml/min, 69 ml/min, and 110 ml/min. The 0.1N, 0.05N, and 0.01N HCl solutions were made isotonic (300 mOsmol) with NaCl. Weight measurements were made at time intervals appropriate for the pH of the solution until the weight was less than 5 mg. pK was calculated from the slope of the linear regression line for each set of data points using the following formula:

$$pK = -\log[1.533 * \text{slope}]$$

3. Results

The results of the six sets of dissolution experiments are tabulated below. Note that a lower pK indicates a faster dissolution rate.

TABLE 4

| Pump Flow Rate (ml/min) | 1N HCl | 0.4N HCl | 0.2N HCl | 0.1N HCl | 0.05N HCl | 0.01N HCl |
|---|---|---|---|---|---|---|
| pKs Resulting from Dissolution of Bolus Using Pump | | | | | | |
| 16 | 0.4190 | 0.8400 | 1.1140 | 1.2390 | 1.5020 | 2.3240 |
| 33 | 0.2710 | 0.5717 | 0.9887 | 1.1524 | 1.4340 | 1.9982 |
| 69 | 0.2392 | 0.4850 | 0.7103 | 1.0674 | 1.2938 | 1.8084 |
| 110 | 0.2069 | 0.4195 | 0.7015 | 0.8288 | 0.9704 | 1.6649 |
| Half-lives (in min) Resulting from Dissolution of Bolus Using Pump | | | | | | |
| 16 | 1.5 | 3.9 | 7.6 | 10.0 | 21.1 | 110.5 |
| 33 | 1.1 | 2.2 | 5.5 | 9.2 | 15.3 | 61.5 |
| 69 | 1.0 | 1.5 | 3.0 | 6.7 | 11.6 | 38.8 |
| 110 | 0.8 | 1.6 | 2.8 | 4.8 | 6.4 | 29.2 |

4. Discussion and Conclusion

The data show an obvious increase in dissolution rate as the pump speed is increased. 110 ml/min was the fastest flow rate that could be attained with this pump, however it is likely that the dissolution rate would continue to increase with a faster pump. The increase in rate may be attributed to the increase in exposure of the bolus to protons. Mechanical removal of surface particles may also play a role.

III. Demineralizing a Calcified Aorta

A. Materials

A human heart with an attached aorta and corotid artery branches was obtained and characterized flouroscopically for the presence of mineralization. The mineralized deposits are radio-opaque and are well-established to be the calcium phosphate mineral carbonated apatite (dahllite) [see Tomasic 1994 In: Brown and Constantz, Hydroxyapatite and Related Materials CRC Press]. Physical manipulation of the tissue indicated that the mineral makes the vessel rigid and the walls of the vessel are hard. Extensive mineralization was seen in the aorta and the three corotid artery branches. Two of the three side branches of the brachial-cephalic corotid artery were completely occluded with mineralization. The other two corotid artery branches were partially occluded with mineralization.

B. Experimental Set-Up

The distal and proximal ends of the aorta were cannulated and tubing was attatched. The distal outflowing tube has a "Y" to allow the exfluent solution to flow into two different collection traps: one for demineralizing solution, the other for saline wash. The reason for this design is that the calcium concentration is measured in the exfluent demineralizing solution so it needs to be isolated from the occasional saline wash to remove contrast media. An infusion catheter was placed through the wall of the proximal tubing and advanced into the aorta to just proximal of the brachio-cephalic corotid branch point. The exfluent ports of the unoccluded corotid arteries and the distal aotric tube were clipped off with hemostats and contrast media was infused into the infusion catheter under fluoroscopy, filling the aorta with radio-opaque contrast media. The extent of occlusion was quantified fluoroscopically. The hemeostats were then unclipped and the system was flushed with saline.

C. Demineralization 4 liters of 1N hydrochloric acid with 0.25 mole/liter sodim chloride concentration were infused through the infusion catheter by drawing the demineralizing solution into 60 ml syringes with lure-lock cannulae, attaching them to the infusion catheter and injecting at a rate ranging between 125 and 250 ml/minute. Four successive infusion segments were performed:

0–5 minutes
5–10 minutes
10–15 minutes
15–20 minutes

Between each five minute infusion the system was flushed with saline, the open exfluent ports were clipped with hemostats, radio-opaque contrast media was infused and the extent of mineralization quantified fluoroscopically. Following this evalution the hemostats were unclipped and the system flushed with saline and the next infusion begun.

D. Results

By the end of the experiment when all four liters of demineralizing solution had been infused, all three totally occluded sub-branches of the brachiocephalic corotids artery had been opened and solution flowed from their distal ports.

1. 0–5 Minutes (Approximately 550 ml)

The solution flowed out of the two partially occluded corotid arteries and the distal aortic tube was clipped off. About 2 minutes into the infusion, solution began dripping from the totally occluded brachio-cephalic segments. When the collected exfluent demineralizing solution was observed, removed solids were collected in a 50 ml centrifuge vial; approximately 20 ccs of solid white material was present. The radio-contrast at 5 minutes showed the occluded arteries opening up and the lumen of all the arteries opening. The general extent of mineralization was also noticeably diminished.

2. 5–10 Minutes (Approximately 1 Liter)

Now the most open corotid artery was clipped off, the partially occluded corotid artery was half clipped off, allowing limited out flow and the distal aortic tube was totally clipped-off. Flow progressively increased from the brachiocorotid arteries and two of the three sub-segments began flowing substantially, as did the partially occluded third corotid artery. Radio-contrast imaging at 10 minutes corroborated the flow observations, showing the arterial lumen had considerably opened to allow flow.

3. 10–15 Minutes (Approximately 1 Liter)

Now both open corotid arteries were clipped off, allowing limited out flow through the brachial-cephalic corotid artery and the distal aortic tube was totally clipped-off. Flow progressively increased from the brachio-corotid artery and two of the three sub-segments began flowing substantially and third sub-segment began flowing somewhat. Radio-contrast imaging at 15 minutes corroborated the flow observations, snowing the arterial lumen had considerably opened to allow flow.

4. 15–20 Minutes (Approximately 1.5 Liters)

Now both open corotid arteries were clipped off as well as the two flowing brachio-cephalic sub-segments, allowing limited out flow through one the brachial-cephalic sub-segment that was most occluded at the beginning and was still only flowing in a restricted fashion. The distal aortic tube was totally clipped-off. Flow progressively increased from the brachio-corotid sub-segment and began flowing to the extent that the flow squirted off the table onto the floor. Radio-contrast imaging at 20 minutes treatment corroborated the flow observations, showing the arterial lumen had considerably opened to allow flow.

E. Conclusion

By the end of the experiment, a heavily calcified aorta and corotid tree was substantially demineralized and flow re-established. The arota changed from being hard to soft and resiltiant to the touch. The vascular tissue showed no mechanical loss of strength of flexible behavior.

IV. Demineralizing Human Cadaveric Leg Arteries—Evaluation of Demineralizing Capabilities The decalcification properties of the demineralizing solution are examined by applying it to in vitro human cadaver vessels. The results are qualitatively analyzed by intravascular ultrasound and contact x-ray imaging while quantitative analysis is performed by atomic absorption spectroscopy.

A. Introduction

In order to evaluate the capabilities of the demineralizing solution, cadaver arteries are perfused with demineralizing solution. Sections of leg vessels from 12 cadavers (fermoral to tibial artery) are obtained with a wide range of calcifications. Intravascular ultrasound and contact x-rays are utilized to qualitatively assess the location and amount of calcification in each vessel prior to perfusion.

B. Demineralizing Procedure

The method for demineralizing the cadaver vessels is designed to realistically simulate the envisioned clinical use of the demineralizing solution. In order to model this, segments of the vessels are sutured to tubing in a water bath and perfused with the one of three different demineralizing solutions for 2 minutes using a peristaltic pump at a flow rate of 50 ml/minute. The demineralizing solutions are: (1) Solution A=1.0 N HCl+0.25 M NaCl; (2) Solution B=.0.5 N HCl+0.25M NaCl; and (3) Solution C=0.1 N HCl+0.05 M NaCl. The demineralizing solution pumped through the vessel is captured in order to quantitate the amount of decalcification.

C. Calcification Analysis

Before and after the demineralizing procedure, intravascular ultrasound is performed with automatic pullback through the vessel and imaging sequences stored to videotape. This ultrasound analysis preserves a video record of the entire length of the vessel which may be qualitatively analyzed for calcium content before and after the procedure. Contact x-rays are also performed for the same purpose and provides a silhouette of the vessel segment. Quantitative decalcification data is obtained by utilizing an atomic absorption spectrometer to measure the calcium concentration in the demineralizing solution captured. By using the stoichiometric formula for the atherosclerotic calcifications, the mass of the material actually removed is calculated.

EXAMPLE V

Infusing Demineralizng Solution Through the Murine Abdominal Aorta—Vascular Response to Demineralizing Solution The following protocol is designed to determine the in vivo cellular response of a vessel to a demineralizing solution developed to treat calcified lesions of the cardiovascular system. This determination of response is accomplished by applying the solution utilized for the decalcification procedure to non-calcified, in vivo rabbit aorta in order to examine the histological response. The demineralizing solution is designed to minimize the cellular damage while still demineralizing vessels effectively; thus, it is believed with a reasonable expectation of success that there will be little or no damage to the vessel tissue.

A. Introduction

In order to evaluate vascular response to the demineralizing solution, 25~male, New Zealand White rabbits (>4 kg) have a segment of their aorta exposed to either a demineralizing solution or a saline control. The segment is isolated from blood by using two standard catheter balloons with a lumen through which the solution may be perfused. The rabbits are then sacrificed after waiting for an established period of time and histology is performed on the aortic segments.

For the initial phase, 27 rabbits are treated, and 3 different concentrations of demineralizing solution are tested along with a saline control. Solutions A, B and C are the same as those employed in Example IV above. The concentration range is chosen with significant chemical differences so that a concentration dependent response is expected. Rabbits from each group are sacrificed at 1, 7, 30 and 90 days. Additionally, 3 rabbits are perfused with saline as controls and sacrificed at 1 (1 rabbit) and 7 days (2 rabbits).

B. Surgical Procedure

On the appropriate day, the selected rabbits are prepared for surgery. The surgical procedure includes the standard anesthesia and physiologic measurement techniques utilized in rabbit studies.

Following preparation, the right or left carotid artery is exposed and carefully incised, and a 5 Fr sheath is inserted. The right or left femoral artery is then exposed and carefully incised, and a 4 or 5 Fr sheath inserted. After 1000U heparin injection (IV), a Schwan-Ganz catheter isnserted via the right or left carotid artery to the abdominal aorta just distal to the renal artery branch under fluoroscopic guidance. A second Schwan-Ganz catheter is inserted via the right or left femoral artery into the abdominal aorta just proximal of the bifurcation of the iliac arteries under fluoroscopic guidance.

Balloon position is monitored angiographically, providing approximately 2 cm section of abdominal aorta for exposure to the demineralizing solution. Following balloon inflation, the isolated environment is rendered substantially bloods by flushing with heparanized saline. Next, sterile demineralizing solution at the scheduled concentration (or the saline control solution) is pumped into the carotid catheter and removed through the femoral catheter by means of a peristaltic pump at a flow rate of 50 ml/minute for 2 minutes. Following this, the region is flushed by pumping 0.9% NaCl through the system for 20 seconds.

C. Euthanasia and Histological Analysis

Rabbits are euthanized at the scheduled postoperative time by a standard intravenous injection. Immediately following euthanasia, the abdominal aorta is harvested and pressure fixed with 10% formalin. Subsequent to fixation, vessels are embedded, sectioned, and stained by a qualified pathologist. Hemotoxylin and eosin (H&E) are used to examine the endothelial and vessel cells, and a trichrome stain is used to examine the connective and collagenous tissue elements. Sections of vessel between catheters (experimental condition) are compared with sections adjacent to the angioplasty balloons (control condition) for the different concentrations of demineralizing solution and control solution. Also, the kidneys, lungs, and liver are frozen for toxicity testing at a later time.

VI. Human Aortic Valve Tests in Vitro

Calcified aortic heart valves are removed operatively during valve replacement surgery and used as an in vitro test system to optimize methods of demineralization. For these studies, a comparison of different acidic treatment solutions is performed. In addition, the acidic treatment solutions are contacted with the calcified aortic valves for varying periods of time. The following solutions and conditions are examined:

| | |
|---|---|
| 0.1 M HCl, | 1.0 M $H_2SO_4$ + 0.1 M EDTA, |
| 1.0 M HCl, | 1.0 M formic acid, |
| concentrated HCl, | concentrated formic acid, |
| 0.1 M HCl + 0.01 M EDTA, | 1.0 M formic acid + 0.1 M EDTA, |
| 1.0 M HCl + 0.01 M EDTA, | 1.0 M acetic acid, concentrated |
| concentrated HCl + 0.1 M EDTA, | acetic acid, |
| 0.1 M $H_2SO_4$, | 1.0 M acetic acid and 0.1 M EDTA, |
| 1.0 M $H_2SO_4$, | 1.0 M succinic acid, |
| 0.1 M $H_2SO_4$ + 0.01 M EDTA, | 1.0 M succinic acid + 0.1 M EDTA. |

Explanted valves are weighed after thorough washing. A flow through system comprising the valves are then prepared and each solution is flowed through the explanted valve. Weight loss is measured at 5, 10, 30, 60, 90 and 120 minutes of incubation in the acidic treatment solution. This experiment is repeated, applying ultrasonic energy at 25 MHz during the flow through period.

During the course of treatment, calcium and phosphate concentration released from the test valves are measured, and rates of demineralization are determined. The valves are evaluated for the extent of remaining biomineralization and the extent of tissue damage (if any) after each experimental protocol. Physiological function tests are also performed following the contact with the acidic treatment solution.

The following parameters are evaluated and optimized alone or in combination: pH, and sonic power. The carbonated apatite of biomineralized heart valve tissue is more soluble under acidic conditions. The pH ranges to be evaluated are below about 7.0, typically below about 4.0, and optimally about 1.0. Sonic power accelerates reactions in solution. Sound frequencies in the range of 20 kHz to 100 kHz are evaluated, typically about 25 kHz.

Prior to and after decalcification, valve insufficiency is evaluated using a pulse duplicator that measures pressure drop across the valve. In addition, flow rate through the valve is measured to obtain information regarding the cross-sectional area of the valve.

VII. Human Aortic Valve Tests in a Porcine Model

The most common causes of pure aortic stenosis are calcification of bicuspid valves, commissural fusion, degenerative calcification of tricuspid valves, cuspid fibrosis, and postinflammatory calcification of rheumatic origin. Calcified valves removed from human patients are transplanted into pigs. The animals are allowed to recover, and are then subjected to demineralization therapy with the acidic treatment solution. Devices for applying the acidic treatment solution to the stenotic aortic valves are made to either apply to a beating heart or a stopped heart. Devices applied to the beating heart will introduce the acidic treatment solution at a specific temperature and pH in conjunction with sonic power. Devices applied to the stopped heart, or to a bypassed heart which is still beating, will isolate the aortic valve region form the blood stream and circulate and cycle demineralizing solution through the aortic valve region.

The surgeon attempts to create grain boundary separations between individual grains of the carbonated apatite (dahllite), which composes the calcified tissue. Acidic solutions preferentially dissolve the calcium phosphate mineral at grain boundaries. Combined with ultrasonic power, this serves to loosen individual grains without having to dissolve the entire grain. Loose grains are removed with the circulating solution. Organic matrices entombed within the mineralized deposit may shield the mineral phase from the acidic treatment solution, necessitating solutions that are efficient in removing elements of an organic matrix from the grain boundary regions. Thus, one can supplement the acidic treatment solution with proteases, surfactants, detergents, oxidants and the like, at concentration sufficient to remove organic matrix without undue damage to the tissue under treatment. Alternatively, the supplements can be provided in one or more individual solutions and alternated with the acidic treatment solution. The removal of the organic matrix exposes the mineral to subsequent treatment with acidic treatment solution. Various solutions can be suction-pumped through the treated region through tubing. In this embodiment, both in-current and out-current flows are present. The out-current flow carries the cycled solutions, the dissolved ions from the mineral with organic debris, and loose pieces of mineralized deposits which become dislodged from the attached mineralized mass before dissolution of the mineral deposit is complete. Different solutions are cycled through the test region from a single site outside the body. Progression of demineralization is monitored using standard echocardiographic methods.

Following the above protocol, the animals are sacrificed and the heart valves are subjected to histological examination and further assays for mineral content.

VIII. Formulations (A) Solution A=1.0 N HCl+0.25 M NaCl.
(B) Solution B=0.5 N HCl+0.25M NaCl.
(C) Solution C=0.1 N HCl+0.05 M NaCl.
(D) A suitable formulation for acidic treatment under a constant flow rate comprises:
  Formic acid (concentrated) . . . 0.10%
  Sodium dodecyl sulfate (SDS) . . . 0.1%
  $H_2O$ . . . qs . . . 100%
(E) An alternative formulation for acidic treatment under a constant flow rate comprises:
  HCl (concentrated) . . . 0.10%
  EDTA . . . 0.1%
  $H_2O$ . . . qs . . . 100%
(F) An alternative formulation for acidic treatment under a constant flow rate comprises:
  Phosphoric acid (concentrated) . . . 10%
  $H_2O$ . . . qs . . . 100%
(G) An alternative formulation for acidic treatment under a constant flow rate comprises:
  Sulfuric acid (concentrated) . . . 10%
  $H_2O$ . . . qs . . . 100%
(H) An alternative formulation for acidic treatment under a slower rate or under static conditions comprises:
  Tris HCl . . . 0.1 M
pH adjusted to 4.2 with concentrated HCl.

IX. The Sheep Model

To evaluate the efficacy of an acidic treatment solution in vivo, a sheep model is utilized. In this model, porcine aortic valved conduits are treated with 0.625% glutaraldehyde in vitro, and transplanted into the descending thoracic aorta in juvenile sheep (see Chanda, J., et al., 1997, Biomaterials 18:1317–1321, herein incorporated by reference). The calcification of the transplanted porcine valves are then analyzed by gross inspection, radiography, light, transmission, and surface scanning electron microscopy, or calcium analysis by absorption spectroscopy can be performed (see Schoen, F. J., et al., 1994, J. Thorac. Cardiovasc. Surg. 108:880–887). Any tissue damaged is also assessed by light microscopy.

A standard open chest surgical procedure is employed where the animal is put on cardiopulmonary bypass and the device shown in FIG. 4 is inserted into the aorta and into the valve. The valve is then contacted with Solution A describe supra, and the demineralization of the calcified valve is determined.

X. Cadaver Study

Human coronary arteries are harvested from heart transplants. Contact x-rays are taken to document the extent and distribution of the mineralized lesions in the harvested arteries. The arteries are ligated at either end to 5 mm polypropylene tubing and a pumping means is employed to produce a flow through device. A carbonic acid solution having a pH of 2.5 to 3.0 is flowed through the artery for a period of 20 minutes. During this period, intravascular ultrasound (IVUS) is employed to monitor the lesion in real time. The carbonic acid solution that has passed through the artery is collected and analyzed for dissolved calcium content using standard analytical methods. A graph is plotted of the mineral content of the collected solution vs. time. Following treatment, a second contact X-ray is taken to assess the extent of the mineralized lesion remaining in the artery. Finally, an ash weight test is performed of the remaining mineral. It is observed in the above assays that flowing a carbonic acid solution through the coronary artery reduces the mineral content of the lesion in the artery. Additional arteries are assayed according to the above methods, with the difference being that flow through times of 30, 60, 90 and 120 minutes are employed.

XI. Rabbit Study

To compare the effect of using a carbonic acid dissolution solution according to the subject invention with the effect of mechanical debridement as produced by a balloon catheter on arterial tissue, the following experiments are performed. Three groups of New Zealand white rabbits are formed, 5 rabbits per group. In each group, the right femoral and iliac arteries are treated with a first treatment method (either dissolution fluid or mechanic debridement) and the left iliac or femoral arteries are treated with another method or left untreated to serve as a control. The following table summarizes the treatment protocols.

| Group | Right Arteries | Left Arteries |
| --- | --- | --- |
| 1 | solution | (−) control |
| 2 | solution | (+) mechanical debridement |
| 3 | (+) mechanical debridement | (−) control |

Following 1, 7, 30 & 90 days, the animals are sacrificed and the illiac and femoral arteries harvested for analysis. The arteries are histographically analyzed for evidence of mechanical insult response and the presence of smooth epithelial cells. It is expected that the solution treated arteries appear similar to the control arteries, while the arteries subject to mechanical debridement show a mechanical insult response.

It is evident from the above results and discussion that improved methods of treating a host suffering from a vascular disease characterized by the presence of a calcified lesion are provided. The subject methods can be performed in a minimally invasive manner, thereby providing all of the advantages attendant therewith, such as reduced trauma to the patient and faster healing times. As the subject methods do not mechanically damage the vascular tissue of the patient, complications such a restinosis are avoided. Furthermore, the subject methods provide an effective and efficient means for removing calcified lesions from vascular tissue. In addition, the subject methods can be used in conjunction with additional treatment modalities, thereby improving the outcome realized with such modalities. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for treating a host suffering from a vascular disease, said method comprising:

flushing a vascular lesion with an acidic dissolution fluid having a pH that does not exceed about 3 to treat said host.

2. The method according to claim 1, wherein said method further comprises applying energy to said calcified lesion in a manner sufficient to breakup said lesion into particles.

3. The method according to claim 1, wherein said method further comprises rendering a local environment of said vascular lesion substantially bloodless.

4. The method according to claim 1, wherein said acidic dissolution fluid comprises an organic or inorganic acid.

5. The method according to claim 4, wherein said acidic dissolution fluid is a hydrochloric acid solution.

6. The method according to claim 4, wherein said acidic dissolution fluid is hypertonic.

7. A system for flushing a vascular tissue site with a dissolution fluid, said system comprising:

(a) a catheter comprising an acidic dissolution fluid introduction lumen capable of delivering fluid to said vascular tissue site and a fluid removal lumen capable of removing fluid and lesion debris from said vascular tissue site, wherein said catheter is in fluid communication with an acidic dissolution fluid source comprising an acidic dissolution fluid having a pH that does not exceed about 3;

(b) a first pumping means operatively linked to said fluid introduction lumen in a manner sufficient such that said first pumping means forces fluid out of the distal end of said fluid introduction lumen; and (c) a second pumping means operatively linked to said fluid removal lumen in a manner sufficient such that said second pumping means sucks fluid into the distal end of said fluid removal lumen.

* * * * *